(12) United States Patent
Lindner et al.

(10) Patent No.: US 10,265,644 B2
(45) Date of Patent: Apr. 23, 2019

(54) ENANTIOSELECTIVE ZWITTERIONIC ION-EXCHANGE MATERIAL

(71) Applicant: UNIVERSITAET WIEN, Vienna (AT)

(72) Inventors: Wolfgang Lindner, Klosterneuburg (AT); Michael Laemmerhofer, Tubingen (DE); Christian Hoffman, Weil am Rhein (DE)

(73) Assignee: UNIVERSITAET WIEN, Vienna (AT)

(*) Notice: Subject to any disclaimer, the term of this patent is extended or adjusted under 35 U.S.C. 154(b) by 246 days.

(21) Appl. No.: 15/056,774

(22) Filed: Feb. 29, 2016

(65) Prior Publication Data
US 2016/0193547 A1 Jul. 7, 2016

Related U.S. Application Data

(63) Continuation of application No. 12/992,558, filed as application No. PCT/AT2009/000192 on May 11, 2009.

(30) Foreign Application Priority Data

May 13, 2008 (EP) .................................. 08450076

(51) Int. Cl.
*B01D 15/36* (2006.01)
*B01J 20/29* (2006.01)
(Continued)

(52) U.S. Cl.
CPC .......... *B01D 15/364* (2013.01); *B01J 20/286* (2013.01); *B01J 20/29* (2013.01); *B01J 20/3219* (2013.01);
(Continued)

(58) Field of Classification Search
CPC ... B01J 41/04; B01J 41/05; B01J 41/07; B01J 41/20; B01J 39/04; B01J 39/26;
(Continued)

(56) References Cited

U.S. PATENT DOCUMENTS

2005/0131087 A1 6/2005 Lindner et al.
2007/0241056 A1 10/2007 Klipper et al.
2011/0121229 A1 5/2011 Lindner et al.

FOREIGN PATENT DOCUMENTS

CN 101069860 A 11/2007
WO WO9746557 12/1997
(Continued)

OTHER PUBLICATIONS

Antal Peter "Direct high-performance liquid chroamatographic enantioseparation of apolar beta-amino acids on a quinine-derived chiral anion-exchanger stationary phaste" Journal of Chromatography A., vol. 955, 2002, pp. 141-150.
(Continued)

*Primary Examiner* — Katherine Zalasky
(74) *Attorney, Agent, or Firm* — Workman Nydegger

(57) ABSTRACT

An enantioselective zwitterionic ion-exchange material comprising a chiral selector component (SO) comprising at least one cation exchange group and at least one anion exchange group and a carrier, carrying said selector component, wherein
the chiral selector component comprises at least one chiral linker moiety to connect said ion exchange groups in a non-macrocyclic fashion, and
said chiral linker moiety contains at least one π-π interaction site.

15 Claims, 6 Drawing Sheets

(51) Int. Cl.
  *B01J 20/32* (2006.01)
  *B01J 39/04* (2017.01)
  *B01J 39/26* (2006.01)
  *B01J 43/00* (2006.01)
  *B01J 20/286* (2006.01)
  *B01J 41/20* (2006.01)
  *B01J 41/04* (2017.01)
  *G01N 1/34* (2006.01)

(52) U.S. Cl.
  CPC ....... *B01J 20/3251* (2013.01); *B01J 20/3253* (2013.01); *B01J 20/3255* (2013.01); *B01J 20/3285* (2013.01); *B01J 39/04* (2013.01); *B01J 39/26* (2013.01); *B01J 43/00* (2013.01); *G01N 1/34* (2013.01); *B01J 2220/54* (2013.01); *B01J 2220/58* (2013.01)

(58) Field of Classification Search
  CPC ........... B01J 39/07; B01J 43/00; B01D 15/08; B01D 15/36; B01D 15/361; B01D 15/364; B01D 15/368; G01N 30/48; G01N 30/482; G01N 30/96; G01N 2030/484
  See application file for complete search history.

(56) References Cited

FOREIGN PATENT DOCUMENTS

WO  WO0027496  5/2000
WO  WO03068397  8/2003

OTHER PUBLICATIONS

Berkecz, et al., "High-performance liquid chromatographic enantioseparation of B-amino acid stereoisomers on a (+)-(18-crown-6)-2,3,11,12-tetracarboxylic acid-based chiral stationary phase," Journal of Chromatography A 1125 (2006) 138-143.

Berkecz, et al., "LC Enantioseparation of B-Lactam and B-Amino Acid Stereoisomers and a Comparison of Macrocyclic Glycopeptide- and B-Cyclodextrin-Based Columns," Chromatographia 63 (2006) S37-S43.

Bicker, "Enantiomeric impurity profiling in ephedrine samples by enantioselective capillary electrochromatography," Electrophoresis 24 (2003) 2532-2542.

Constantin, et al., "Enantioselective strong cation-exchange molecular recognition materials: Design of novel chiral stationary phases and their application for enantioseparation of chiral bases by nonaqueous capillary electrochromatography," Electrophoresis 24 (2003) 1668-1679.

Cordero, et al., "Amino-Sulfonation of Alkenes in a Three-Component Reaction," Eur. J. Org. Chem. (2002) 1407.

Czerwenka, et al., "Structure-enantioselectively relationships for the study of chiral recognition in peptide enantiomer separation on cinchona alkaloid-based chiral stationary phases by HPLC: Influence of the N-terminal protecting group," J. Sep. Sci. 26 (2003) 1499.

Davankov, "Chiral selectors with chelating properties in liquid chromatography: fundamental reflections and selective review of recent developments," Journal of Chromatography A 666 (1994) 55.

Davankov, et al., "Separation of Unmodified Amino Acid Enantiomers by Reverse Phase HPLC," Chromatographia 13 (1980) 677-685.

Ernst Tobler Investigation of an enantioselective non-aqueous capillary electrochromatography system applied to the separation of chiral acids: Journal of Chromatography A., vol. 875, 2000, pp. 341-352.

Franco, et al., "A comparative evaluation of random and site-specific immobilization techniques for the preparation of antibody-based chiral stationary phases," J. Sep. Sci. 29 (2006) 1458-1469.

Franco, et al., "Novel cinchona alkaloid carbamate C9-dimers as chiral anion-exchange type selectors for high-performance liquid chromatography," Journal of Chromatography A 869 (2000) 111-127.

Gika, et al., "Direct separation and quantitative analysis of thyroxine and triiodothyronine enantiomers in pharmaceuticals by high-performance liquid chromatography," Journal of Chromatography B 800 (2004) 193-201.

Gyimesi-Forrás, "Enantiomer Separation of a Powerful Chiral Auxiliary, 2-Methoxy-2-(1-naphthyl) propionic Acid by Liquid Chromatography Using Chiral Anion Exchanger-Type Stationary Phases in Polar-Organic Mode; Investigation of Molecular Recognition Aspects," Chirality 17 (2005) S134-S142.

Haginaka, "Protein-based chiral stationary phases for high-performance liquid chromatography enantioseparations," Journal of Chromatography A 906 (2001) 253-273.

Hebenstreit, et al., "Novel enantioselective strong cation exchangers based on sulfodipeptide selectors: Evaluation for enantiomer separation of chiral bases by nonaqueous capillary electrochromatography," Electrophoresis 25 (2004) 277-289.

Hoffmann, et al., "Novel strong cation-exchange type chiral stationary phase for the enantiomer separation of chiral amines by high-performance liquid chromatography," Journal of Chromatography A 1161 (2007) 242-251.

Hu, et al., "Electrostatic Ion Chromatography," Analytical Chemistry 65 (1993) 2204-2208.

Hu, et al., "Electrostatic ion chromatography," Trac-Trends in Analytical Chemistry 17 (1998) 73-79.

Hu, et al., "Electrostatic Ion Chromatography. 2. Partitioning Behaviors of Analyte Cations and Anions," Analytical Chemistry 66 (1994) 2514-2520.

Hu, et al., "Simultaneous Separation of Inorganic Cations and Anions by Ion Chromatography Using a Single Column Coated with Weak/Strong-Charged Zwitterionic Bile Salt Micelles," Analytical Chemistry 66 (1994) 765-767.

Hyun, "Characterization of liquid chromatographic chiral separation on chiral crown ether stationary phases," J. Sep. Sci. 26 (2003) 242-250.

Hyun, et al., "Liquid chromatographic resolution of racemic amino acids and their derivatives on a new chiral stationary phase based on crown ether," Journal of Chromatography A 822 (1998) 155-161.

Ilisz, et al., "HPLC separation of amino acid enantiomers and small peptides on macrocyclic antibiotic-based chiral stationary phases: A review," J. Sep. Sci. 29 (2006) 1305-1321.

Jiang, et al., "Zwitterionic stationary phase with covalently bonded phosphorylcholine type polymer grafts and its applicability to separation of peptides in the hydrophilic interaction liquid chromatography mode," Journal of Chromatography A 1127 (2006) 82-91.

Kricheld.Hr, "Uber die Silylierung von Aminosauren und die Peptidsynthese mit Aminosaurentrimethylsilylestern," Annalen Der Chemie-Justus Liebig 763 (1972) 17.

Lämmerhofer, et al., "Liquid Chromatographic Enantiomer Separation and Chiral Recognition by Cinchona Alkaloid-Derived Enantioselective Separation Materials," CRC Ress, Taylor & Francis Group, Boca Raton, 2008.

Lämmerhofer, et al., "Quinine and quinidine derivatives as chiral selectors I. Brush type chiral stationary phases for high performance liquid chromatography based on cinchonan carbamates and their application as chiral anion exchangers," Journal of Chromatography A 741 (1996) 33-48.

Maier, et al. "Separation of enantiomers: needs, challenges, perspectives," Journal of Chromatography A 906 (2001) 3-33.

Mandl, et al., "Quinine versus carbamoylated quinine-based chiral anion exchangers A comparison regarding enantioselectively for N-protected amino acids and other chiral acids," Journal of Chromatography A 858 (1999) 1-11.

Nesterenko, et al., "Selectivity of chemically bonded zwitterions-exchange stationary phases in ion chromatography," Journal of Chromatography A 706 (1995) 59-68.

Nesterenko, et al., "Zwitterionic Ion-Exchangers in Liquid Chromatography," Analytical Sciences 16 (2000) 565-574.

Nogueira, et al., "Spectrophotometric determination of sulfhydryl concentration on the surface of thiol-modified chromatorgraphic

(56) References Cited

OTHER PUBLICATIONS silica particles using 2,2'-dipyridyl disulfide reagent," Analytica Chimica Acta 533 (2005) 179-183.

Peter, et al., Journal of Peptide Science 12 (2006) 234. (Symposium abstract! Contents of this abstract is described in paper: Sztojkov-Ivanov, A., Lazar, L., Fulop, F., Armstrong, D. W., and Peter, A. Chromatographia 2006, 64, 89-94).

Preinerstorfer, et al., "Monolithic silica-based capillary column with strong chiral cation-exchange type surface modification for enantioselective non-aqueous capillary electrochromatography," Journal of Chromatography A 1106 (2006) 94-105.

Preinerstorfer, et al., "Polymethacrylate-type monoliths functionalized with chiral amino phosphonic acid-derived strong cation exchange moieties for enantioselective nonaqueous capillary electrochromatography and investigation of the chemical composition of the monolithic polymer," Electrophoresis 26 (2005) 2005.

Sardella, et al., "Enantioselective HPLC of Potentially CNS-Active Acidic Amino Acids with a Cinchona Carbamate Based Chiral Stationary Phase," Chirality 20 (2008) 571-576.

Sztojkov-Ivanov, et al., "Comparison of Separation Efficiency ofMacrocyclic Glycopeptide-Based Chiral Stationary Phases for the LC Enantioseparation of B-Amino Acids," Chromatographia 64 (2006) 89-94.

Tobler, et al., "Low-molecular-weight chiral cation exchangers: Novel chiral stationary phases and their application for enantioseparation of chiral bases by nonaqueous capillary electrochromatography," Electrophoresis 23 (2002) 462-476.

Viklund, et al., "Chromatographic Interactions between Proteins and Sulfoalkylbetaine-Based Zwitterionic Copolymers in Fully Aqueous Low-Salt Buffers," Analytical Chemistry 73 (2001) 444-452.

Wang, et al., "Empirical Observations and Mechanistic Insights on the First Boron-Containing Chiral Selector for LC and Supercritical Fluid Chromatography," Analytical Chemistry 79 (2007) 8125.

Yang "Multifunctional ion-exchange stationary phases for high-performance liquid chromatography" Journal of Chromatography A., vol. 722, 1996, pp. 87-96.

Yu, et al., "The Synthesis and Characterization of Chemically Bonded Silica-Based Zwitterion-Exchangers for HPLC," Journal of Chromatographic Science 24 (1986) 177-182.

Yu, et al., "Zwitterionic Stationary Phases in HPLC," Journal of Chromatographic Science 27 (1989) 176-185.

Zarbl, et al., "Strong versus weak chiral cation exchangers: comparative evaluation for enantiomer separation of chiral bases by non-aqueous CEC," J. Sep. Sci. 25 (2002) 1269-1283.

U.S. Appl. No. 12/992,558, filed Feb. 2, 2011, Office Action dated Oct. 15, 2014.

U.S. Appl. No. 12/992,558, filed Feb. 2, 2011, Final Office Action dated Jun. 19, 2015.

U.S. Appl. No. 12/992,558, filed Feb. 2, 2011, Final Office Action dated Oct. 28, 2015.

ENANTIOSELECTIVE ZWITTERIONIC ION-EXCHANGE MATERIAL

CROSS-REFERENCE TO RELATED APPLICATIONS

This application is a continuation of U.S. patent application Ser. No. 12/992,558, filed Feb. 2, 2011, which is a 371 application of International Patent Application No. PCT/AT09/00192, filed May 11, 2009, which claims the benefit if European Application No. 08450076.8, filed May 13, 2008. The disclosures of the foregoing applications are incorporated herein in their entirety.

BACKGROUND

The invention is concerned with an enantioselective zwitterionic ion-exchange material comprising a chiral selector component (SO) comprising at least one cation exchange group and at least one anion exchange group and a carrier, carrying said selector component directly or via a spacer.

In the field of enantioselective chromatography using ion exchanger type chiral stationary phases (CSPs) separation takes place due to enantioselective ion pairing of oppositely charged chiral selectors (SO) and analytes. Conceptually, a chiral molecular recognition process of enantioselective ion pairing could principally occur with every CSP that contains ionizable groups within its chiral selector moieties, may they be part of e.g. a small SO molecule- or of glycopeptide- or protein-based separation materials [1-4]. CSPs that are based on immobilized cinchona alkaloid derivatives as low molecular mass SOs specifically employ the ion pairing process as the primary interaction between SOs and analytes. Thereupon, secondary interactions like for instance H-bond formation and π-π stacking (interaction) can follow and finally lead to enantiodiscrimination. Among this thoroughly investigated class of chiral weak anion exchangers (WAX) the CSPs based on O9-tert-butylcarbamate derivatives of quinine and quinidine as SOs provide excellent enantioseparation capabilities for a broad range of chiral acids [5,6]. FIG. 1a shows the SO structure of a quinine-type WAX CSP which is also commercially available (CHIRAL-PAK QN-AX from Chiral Technologies, France).

Complementary to these WAX type CSPs, also separation materials based on fully synthetic low molecular mass weak and strong cation exchanger (WCX and SCX) SOs have been developed and investigated for the enantioseparation of chiral basic analytes via an ion pairing driven process [7-12]. Exemplarly depicted in FIG. 1b with a chiral sulfonic acid based SO, such cation exchanger CSPs have been applied to different enantioselective separation techniques including capillary electrochromatography (CEC), capillary liquid chromatography (CLC), and high performance liquid chromatography (HPLC) [13]. Only very recently, a more complex but very interesting boronic acid based chiral cation exchanger SO derived from the macrodiolide boromycin was also reported [14] indicating the potential of ion exchangers in enantioselective chromatography.

However, chiral cation and anion exchangers encounter the limitation of addressing only analytes that carry a charge of opposite sign.

Principally, stationary phases containing complementary charged groups have also been described in the literature [15-19] and were applied mainly for the separation of inorganic cations and anions. Systems employing chiral zwitterionic moieties have also been reported previously for different purposes [20-24] but were not envisioned for enantiomer separations.

SUMMARY

It is the object of the present invention to provide for a chromatographic material for efficient enantiomeric separation of a variety of chiralic compounds, such as chiral acids, chiral amines and chiral zwitterionic compounds.

The inventive enantioselective zwitterionic ion-exchange material comprises a chiral selector component (SO) comprising at least one cation exchange group and at least one anion exchange group and a carrier, carrying said selector component, wherein
  the chiral selector component comprises at least one chiral linker moiety to connect said ion exchange groups in a non-macrocyclic fashion, and
  said chiral linker moiety contains at least one π-π interaction site (e.g, an aromatic group with preferentially electron-withdrawing or electron-donating substituents).

The meaning of the term "carrying" comprises the direct linkage of the carrier to the selector component and also the indirect linkage via a spacer. The carrier or support should be inactive (inert) with regard to binding of the target compound, but has the function to guarantee the chemical and physical stability of the molecular recognition material. In flow-through applications like chromatography the carrier, resp. its physical properties, determines the kinetic properties of the materials. The carrier may be an inorganic, organic, or mixed inorganic-organic hybride type material. Such materials comprise commercially available and self-developed beads, monolithic or continuous materials comprising silica, alumina, zirconia, titania, sol-gel derived materials, organic-inorganic siliceous hybrid materials, optionally crosslinked polysiloxanes, anyone of the polymers obtained from vinyl-monomers, optionally crosslinked poly(meth)acrylates, optionally crosslinked poly(meth)acrylamides, optionally crosslinked polystyrenes, mixed styrene-(meth)acrylate polymers, ring-opening methathesis polymers, polysaccharides, agarose, and anyone of these materials specifically functionalized to allow immobilization of the chiral selector component. Amongst the preferred supports are silica beads, poly(meth)acrylate polymer beads, poly(meth)acrylamide beads, poly(meth)acrylate monoliths, polystyrene resins, which optionally are modified with pendant reactive groups for immobilization of the selector, as known in the art.

The spacer has mainly the function to link the selector component to the carrier. Both length and chemical functionality of the spacer are variable. Strategies of immobilization that are preferred include reaction of a vinyl-modified selector with a thiol-modified carrier, in particular thiolpropyl-modified silica, by radical addition reaction. Other immobilization concepts that may be utilized include reaction of a diisocyanate linker asymmetrically with amino or hydroxy alkyl-modified carrier and amino or hydroxyl-modified selector component, reaction of amino, hydroxyl, or thiol-modified carrier with chloro- or bromoalkanoyl-derivatized selector, reaction of alkoxy- or chloroorganosilane with terminal reactive functionality for coupling to the selector component, hydrosylation reaction of alkoxy- or chlorohydrosilane with vinyl-group containing selector etc.

The chiral linker moiety that connects the ion exchange groups is a chiral compound in a single enantionmeric form or is constructed from enantiomerically pure chiral synthons like natural or non-natural, cyclic or non-cyclic amino acids, hydroxyl carboxylic acids, amino phosphonic acids, amino phosphinic acids, amino sulfonic acids, amino sulfinic acids, amino boronic acids, hydroxy phosphonic acids, mercapto phosphonic acids, tartaric acid derivatives, mandelic acid derivatives, camphor sulfonic acid derivatives, linear or cyclic natural and non-natural peptides, linear or cyclic sulfopeptides, linear or cyclic phosphono peptides.

A preferred enantioselective zwitterionic ion-exchange material is characterized in that said at least one cation exchange group has a pka<5.5, preferably <3.0, and said at least one anion exchange group has a pka>8.0, preferably >8.0.

A further preferred embodiment of the inventive enantioselective zwitterionic ion exchange material contains a selector compound SO containing at least two acidic groups with pka values <5.5 and at least one basic group with pka>8.0.

The selector compound SO contains more preferred at least two basic groups with pka values >8.0 and at least one acid group with a pka<5.5.

The cation exchange group is e.g. a carboxylic, sulfonic, sulfinic, phosphoric, phosphonic or phosphinic group.

The anion exchange group is e.g. a primary, secondary, tertiary or quarternary amino group.

More preferred the anion exchange group is a quinine or quinidine residue, and the cation exchange group is a sulfonic acid group.

The present invention relates also to all chromatographic techniques that utilize the enantioselective zwitterionic ion-exchange material according to the present invention, e.g. preparative solid-liquid or liquid-liquid chromatographic methods, solid-liquid or liquid-liquid extraction technologies, and membrane separation techniques. In analogy, their use in analytical methodologies integrated as adsorption materials in column liquid chromatography, supercritical fluid chromatography, capillary electrochromatography, chip technologies or as molecular recognition materials and sensitive layers in sensor technologies is also subject of the present invention.

DETAILED DESCRIPTION OF THE INVENTION

Figure 2:
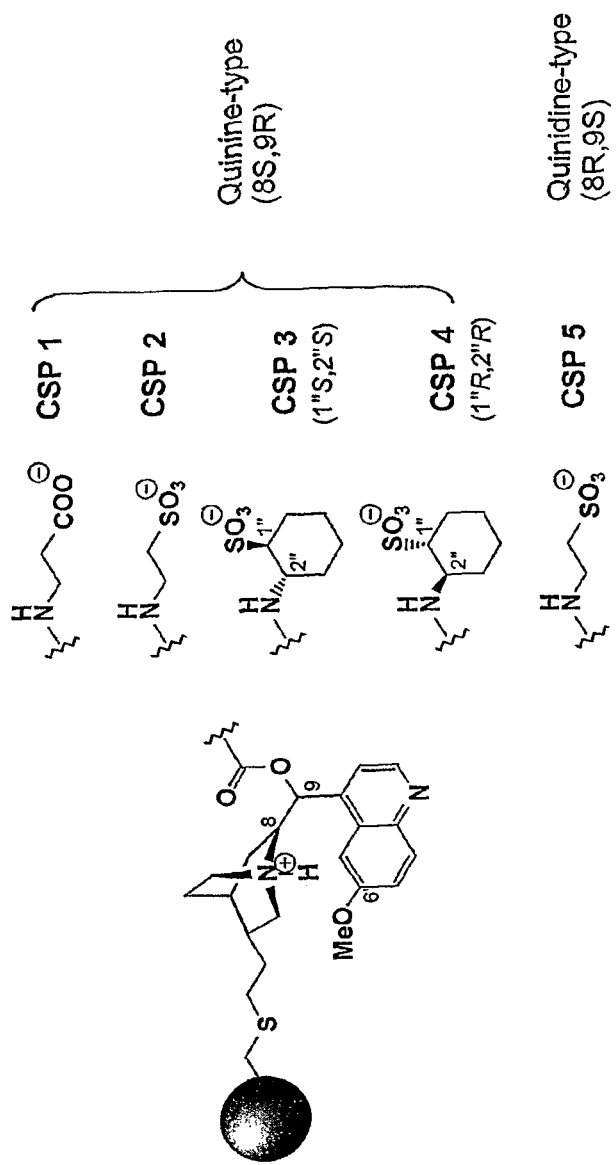
FIG. 2 shows novel zwitterionic SOs and corresponding CSPs 1-5.

In order to demonstrate the enantioselective chromatography of chiral acidic and basic solutes using only one but zwitterionic selector motif, the design, the synthesis and the evaluation of novel zwitterionic SOs and their corresponding CSPs 1-5, as shown in FIG. 2, will be described in the following. Furthermore, such zwitterionic SOs allow also for an enantioselective molecular recognition process of zwitterionic solutes like amino acids and peptides which relies on simultaneous double ion pairing. Direct amino acid enantiomer separations have already been reported for glycopeptide-, crown ether-, CLEC-type CSPs [25-32] and for QN-AX on a selected application [33,34], but all are based on different molecular interaction principles. Nevertheless, chromatographic enantiomer separations of alpha-, beta- and gamma-amino acids is still a challenging task where the zwitterionic SO approach could provide a novel and promising perspective. Overall, in the following preferred zwitterionic CSPs 1-5 were evaluated in polar organic mobile phase conditions for their enantioseparation capabilities not only towards chiral acids and chiral amines but also for chiral zwitterionic analytes like amino acids and dipeptides.

General Information

All chemical reactions were carried out under anhydrous conditions using nitrogen atmosphere and oven-dried glassware unless otherwise stated. $^1$H and $^{13}$C NMR spectra were acquired on a Bruker DRX 400 MHz spectrometer. The chemical shifts (δ) are given in parts per million (ppm) using tetramethylsilane as internal standard. Mass spectrometry was performed on a PESciex API 365 triple quadrupole mass spectrometer (Applied Biosystems/MDS Sciex, Concord, Canada) equipped with a standard electrospray source. Specific optical rotation values were measured at 20° C. on a Polarimeter 341 from PerkinElmer (Vienna, Austria). Elemental analysis was carried out with an EA 1108 CHNS—O from Carlo Erba. Thin-layer chromatography was performed with TLC aluminium sheets Silica gel 60 $F_{254}$ from Merck (Darmstadt, Germany). Flash chromatography was carried out using Silica 60 (0.040-0.063 mm particle size) from Merck (Darmstadt, Germany).

Materials

Thiol-modified silica gel was prepared from spherical silica gel (Daisogel 120-5, pore size 120 Å, particle size 5 μm, from Daiso Chemical Co., Ltd., Japan), similar to a previously published procedure [35]. Thiol-group grafting level of 940 μmol/g was assessed by a spectrophotometric assay employing 2,2'-dithiodipyridine [36]. Trans-2-aminocyclohexanesulfonic acid was prepared according to published procedures [13,37]. All chemicals used for synthesis were of reagent grade quality or higher, purchased from Sigma-Aldrich (Vienna, Austria) and were used without further purification except the following: dichloromethane (Sigma-Aldrich, Austria) was distilled over calcium hydride prior to use, and quinine was bought from Buchler (Braunschweig, Germany). Methanol and acetonitrile as solvents for HPLC were of HPLC-grade from Merck (Darmstadt, Germany) Mobile phase additives acetic acid (HOAc), formic acid (FA), diethylamine (DEA), and ammonium acetate (NH$_4$OAc) were of analytical grade (Sigma-Aldrich, Austria). The chiral basic analytes and zwitterionic amino acid analytes used here were either commercially available or were kind gifts from research partners. N-blocked amino acids as acidic analytes were either commercially available or synthesized according to literature procedures [38].

Instrumentation

Chromatographic measurements were performed on a 1100 Series HPLC system from Agilent Technologies (Waldbronn, Germany) consisting of a solvent degasser, a pump, an autosampler, a column thermostat and a multi-wavelength UV-Vis detector for detection of analytes containing a chromophore sufficient for UV detection. For analytes with weak UV absorbance properties, a Corona® charged aerosol detector (CAD®) from ESA Biosciences, Inc. (Chelmford, USA) was used instead. Whether UV or CAD detection was applied for the data shown in figures and tables will be specifically stated in the legends. Data aquisition and analysis was carried out with ChemStation® chromatographic data software from Agilent Technologies. To assess the elution order of selected solute enantiomers, either single enantiomers of known absolute configuration or specifically enantioenriched samples were injected or an a Jasco OR-990 optical rotation detector (Jasco, Gross-Umstadt, Germany) was used online. Elution was performed in isocratic mode at a mobile phase flow rate of 1 ml/min. If not otherwise stated, column temperature was 25° C. UV detection was accomplished at selected wavelengths between 230 and 280 nm. The void volumes of the columns were determined by injecting acetone with detection at 280 nm. All analytes were applied as methanolic solutions of 0.5-1.0 mg/ml.

Figure 3:
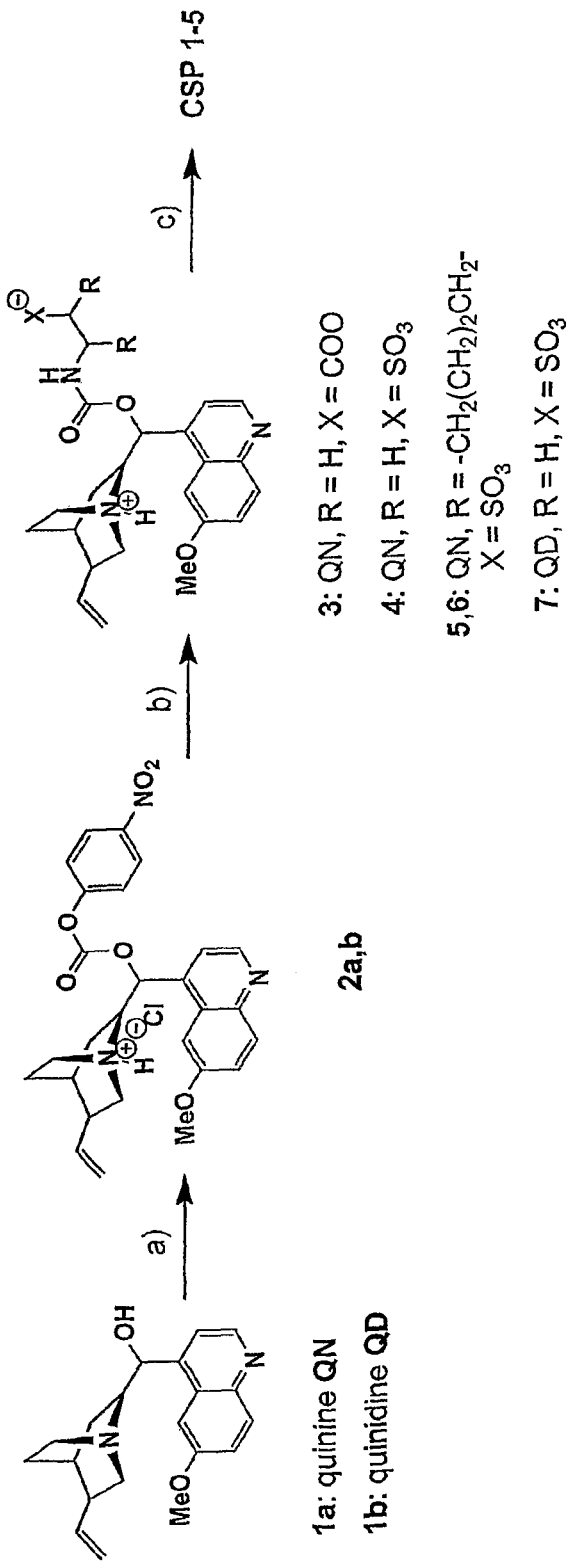
FIG. 3 shows the synthesis of zwitterionic, cinchona-based CSPs 1-5.

Synthesis of Zwitterionic, Cinchona-Based CSPs 1-5 (FIG. 3)

General Procedure for Cinchona Activation [39].

Typically, cinchona alkaloid 1 (5.0 g, 10 mmol) was dissolved in toluene (150 ml) and the solution was dried azeotropically using a Dean-Stark apparatus. After cooling to ambient temperature, 4-nitrophenyl chloroformate (2.0 g, 11 mmol) was added portionwise. The resulting mixture was stirred overnight. A pale yellow precipitate formed which was collected by filtration. Washing with n-hexane (3×50 ml) and drying under reduced pressure yielded 2 as a pale yellow solid (7.0 g, almost quantitative yield) that was used in the next step without further purification.

O9-(4-Nitrophenyl)oxycarbonyl quinine hydrochloride 2a. MS (ESI, positive): 490.5 [M+H]$^+$, 979.5 [2M+H]$^+$.

O9-(4-Nitrophenyl)oxycarbonyl quinidine hydrochloride 2b. MS (ESI, positive): 490.5 [M+H]$^+$, 979.5 [2M+H]$^+$.
General Procedure for the Preparation of Zwitterionic SOs 3-7.

Typically, N, O-bis(trimethylsilyl)acetamide BSA (4.0 ml, 12 mmol) was added portionwise to a suspension of finely grounded amino acid (4.0 mmol) in dry $CH_2Cl_2$ (80 ml). The resulting mixture was stirred and heated under reflux until a clear solution was formed (up to 36 h). After cooling to ambient temperature, activated cinchona alkaloid 2 (2.5 g, 4.1 mmol) was added portionwise and the solution was stirred overnight while becoming slightly yellow. After quenching with MeOH (2 ml), the reaction mixture was directly transferred to a bed of silica gel (150 g) which was preequilibrated with $CH_2Cl_2$. Purification by flash chromatography ($CH_2Cl_2$/MeOH 20/1 to 5/1) yielded the zwitterionic SO.

N-[[[(8S,9R)-6'-methoxycinchonan-9-yl]oxy]carbonyl]-β-alanine 3

91%, pale brown solid. $^1$H NMR [$CD_3OD$]: δ=8.68 (d, 1H), 7.97 (d, 1H), 7.55 (d, 1H), 7.53 (d, 1H), 7.45 (dd, 1H), 6.93 (d, 1H), 5.75 (m, 1H), 5.09 (d, 1H), 5.01 (d, 1H), 4.02 (s, 3H), 3.75 (m, 1H), 3.64 (m, 1H), 3.53 (m, 1H), 3.48-3.33 (m, 2H), 3.27-3.14 (m, 2H), 2.73 (m, 1H), 2.47 (m, 2H), 2.21-2.08 (m, 2H), 2.03 (m, 1H), 1.84 (m, 1H), 1.71 (m, 1H). $^{13}$C NMR: δ=176.6 (COOH), 160.4 ($C_{ar}$), 156.2 (C=O), 148.1 ($C_{ar}$H), 145.0 ($C_{ar}$), 143.6 ($C_{ar}$), 139.4 (CH=), 131.8 ($C_{ar}$H), 127.4 ($C_{ar}$), 123.9 ($C_{ar}$H), 119.7 ($C_{ar}$H), 117.1 ($CH_2$=), 102.5 ($C_{ar}$H), 71.4 (CH), 59.8 (CH), 57.1 (OMe), 55.7 ($CH_2$), 44.8 ($CH_2$), 38.6 (CH), 38.5 ($CH_2$), 36.1 ($CH_2$), 28.3 (CH), 25.2 ($CH_2$), 20.9 ($CH_2$). MS (ESI, positive): 440.4 [M+H]$^+$, 462.4 [M+Na]$^+$, 879.6 [2M+H]$^+$, 901.5 [2M+Na]$^+$.

N-[[[(8S,9R)-6'-methoxycinchonan-9-yl]oxy]carbonyl]-taurine 4

55%, pale yellow solid. $^1$H NMR [$CD_3OD$]: δ=8.73 (d, 1H), 8.00 (d, 1H), 7.64 (d, 1H), 7.50 (s, 1H), 7.48 (d, 1H), 6.94 (s, 1H), 5.78 (m, 1H), 5.14 (d, 1H), 5.05 (d, 1H), 4.05 (s, 3H), 3.87-3.74 (m, 2H), 3.65 (m, 2H), 3.50 (m, 1H), 3.37 (m, 2H), 3.01 (m, 2H), 2.84 (m, 1H), 2.30-2.19 (m, 2H), 2.13 (m, 1H), 1.99 (m, 1H), 1.75 (m, 1H). $^{13}$C NMR: δ=160.5 ($C_{ar}$), 155.9 (C=O), 147.8 ($C_{ar}$H), 144.4 ($C_{ar}$), 143.6 ($C_{ar}$), 138.9 (CH=), 131.4 ($C_{ar}$H), 127.4 ($C_{ar}$H), 124.3 ($C_{ar}$H), 119.5 ($C_{ar}$H), 117.4 ($CH_2$=), 102.3 ($C_{ar}$H), 71.1 (CH), 60.0 (CH), 57.1 (OMe), 55.8 ($CH_2$), 51.5 ($CH_2$), 45.5 ($CH_2$), 38.4 ($CH_2$), 38.3 (CH), 28.2 (CH), 25.0 ($CH_2$), 20.7 ($CH_2$). MS (ESI, positive): 476.4 [M+H]$^+$, 498.4 [M+Na]$^+$. MS (ESI, negative): 474.2 [M−H]$^-$.

Chromatographic separation of the diastereomers (see below) gave highly pure 5 and 6.

trans-(1"S,2"S)—N-[[[(8S,9R)-6'-methoxycinchonan-9-yl]oxy]carbonyl]-2"-aminocyclo-hexanesulfonic acid 5

64%, off white crystals. $^1$H NMR [$CD_3OD$]: δ=8.70 (d, 1H), 7.95 (d, 1H), 7.60 (d, 1H), 7.40 (dd, 1H), 7.30 (d, 1H), 6.85 (s, 1H), 5.77 (m, 1H), 5.23 (d, 1H), 5.04 (d, 1H), 4.03 (m, 1H), 3.92 (s, 3H), 3.81 (m, 1H), 3.73 (m, 2H), 3.38 (m, 1H), 2.85 (s, 1H), 2.70 (m, 1H), 2.39 (m, 1H), 2.31 (m, 1H), 2.21 (m, 1H), 2.12 (s, 1H), 1.95 (m, 2H), 1.85-1.68 (m, 3H), 1.52 (m, 1H), 1.30 (m, 4H). $^{13}$C NMR: δ=160.3 ($C_{ar}$), 155.6 (C=O), 148.2 ($C_{ar}$H), 145.0 ($C_{ar}$), 143.1 ($C_{ar}$), 139.2 (CH=), 131.9 ($C_{ar}$H), 127.1 ($C_{ar}$), 123.6 ($C_{ar}$H), 119.9 ($C_{ar}$H), 117.3 ($CH_2$=), 102.2 ($C_{ar}$H), 71.0 (CH), 63.6 (CH), 60.0 (CH), 56.5 (OMe), 56.0 ($CH_2$), 53.2 (CH), 46.1 ($CH_2$), 38.5 (CH), 35.0 ($CH_2$), 29.4 ($CH_2$), 28.2 (CH), 26.1 (2×$CH_2$), 25.3 ($CH_2$), 20.8 ($CH_2$). MS (ESI, positive): 530.5 [M+H]$^+$, 552.3 [M+Na]$^+$, 1059.7 [2M+H]$^+$, 1081.7 [2M+Na]$^+$.

trans-(1"R,2"R)—N-[[[(8S,9R)-6'-methoxycinchonan-9-yl]oxy]carbonyl]-2"-aminocyclo-hexanesulfonic acid 6

55%, off white solid. $^1$H NMR [$CD_3OD$]: δ=8.77 (d, 1H), 8.05 (d, 1H), 7.71 (d, 1H), 7.54 (d, 1H), 7.41 (s, 1H), 6.76 (s, 1H), 5.75 (m, 1H), 5.12 (d, 1H), 5.06 (d, 1H), 4.03 (s, 3H), 3.88 (m, 2H), 3.71 (m, 1H), 3.65 (m, 1H), 3.44 (m, 1H), 3.38 (m, 1H), 3.08 (m, 1H), 2.85 (s, 1H), 2.40-2.05 (m, 5H), 1.95 (m, 2H), 1.75 (m, 1H), 1.66 (m, 1H), 1.58 (m, 1H), 1.48 (m, 1H), 1.40-1.19 (m, 2H). $^{13}$C NMR: δ=160.0 ($C_{ar}$), 155.3 (C=O), 148.4 ($C_{ar}$H), 144.4 ($C_{ar}$), 142.7 ($C_{ar}$), 138.7 (CH=), 131.8 ($C_{ar}$H), 126.8 ($C_{ar}$), 123.7 ($C_{ar}$H), 120.2 ($C_{ar}$H), 117.2 ($CH_2$=), 101.9 ($C_{ar}$H), 71.1 (CH), 61.5 (CH), 59.8 (CH), 57.0 (OMe), 55.6 ($CH_2$), 53.4 (CH), 45.4 ($CH_2$), 37.7 (CH), 33.4 ($CH_2$), 29.0 ($CH_2$), 27.5 (CH), 25.8 ($CH_2$), 25.7 ($CH_2$), 24.8 ($CH_2$), 20.7 ($CH_2$). MS (ESI, positive): 530.3 [M+H]$^+$, 552.4 [M+Na]$^+$, 1059.7 [2M+H]$^+$, 1081.7 [2M+Na]$^+$.

N-[[[(8R,9S)-6'-methoxycinchonan-9-yl]oxy]carbonyl]-taurine 7

90%, yellow crystals. $^1$H NMR [$CD_3OD$]: δ=8.79 (d, 1H), 7.96 (d, 1H), 7.78 (d, 1H), 7.56-7.50 (m, 2H), 7.11 (s, 1H), 6.14 (m, 1H), 5.33-5.24 (m, 2H), 4.01 (s, 3H), 3.87 (m, 1H), 3.65-3.51 (m, 5H), 3.37 (m, 1H), 3.02 (m, 2H), 2.77 (m, 1H), 2.42 (m, 1H), 2.06 (m, 1H), 2.02-1.83 (m, 2H), 1.47 (m, 1H). $^{13}$C NMR: δ=161.2 ($C_{ar}$), 155.7 (C=O), 146.8 ($C_{ar}$), 145.8 ($C_{ar}$H), 141.2 ($C_{ar}$), 137.9 (CH=), 128.8 ($C_{ar}$H), 127.9 ($C_{ar}$), 126.1 ($C_{ar}$H), 120.1 ($C_{ar}$H), 118.4 ($CH_2$=), 102.6 ($C_{ar}$H), 71.4 (CH), 59.8 (CH), 57.4 (OMe), 51.5 ($CH_2$), 51.0 ($CH_2$), 50.1 ($CH_2$), 38.5 ($CH_2$), 38.2 (CH), 28.7 (CH), 23.7 ($CH_2$), 20.4 ($CH_2$). MS (ESI, positive): 476.2 $[M+H]^+$, 498.2 $[M+Na]^+$, 951.4 $[2M+H]^+$, 973.4 $[2M+Na]^+$.

HPLC Semipreparative Diastereomer Separation of SO 5 and 6

Isocratic semipreparative chromatographic resolution of diastereomers 5 and 6 was performed with the standard analytical HPLC system described above in combination with a 12/13-switching valve from Agilent Technologies, which was connected to the flow path just behind the UV detector for automated fraction collection. The employed stationary phase was β-alanine-based CSP 1 that was packed in house into a stainless steel column (150×4 mm I.D). As mobile phase 25 mM (0.142%, v/v) HOAc in MeOH was used, the flow was set to 1.0 ml/min, and the column temperature was 25° C. The amino acid diastereomers were dissolved in MeOH at a concentration of 100 mg/ml and were distributed to standard HPLC vials. Sample amounts injected onto the column were 85 µl or 8.5 mg, respectively.

In a series of injections, the diastereomers were separated and collected in two fractions, which were concentrated in vacuo. The purity of the collected diastereomers was assessed analytically using similar conditions (CSP 1; 25 mM HOAc in MeOH). The first eluted diastereomer 5 was assigned the (1"S,2"S)-configuration in the cyclohexanesulfonic acid subunit, and accordingly, the second eluted diastereomer 6 the (1"R,2"R)-configuration. Basis of these assignments are preliminary X-ray crystallographic data on 5.

SO Immobilization and Column Packing

General Procedure for the Preparation of Zwitterionic SO-Based CSPs.

Typically, oven-dried thiol-modified silica gel (2.20 g) was suspended in MeOH (10 ml). SO (380 mg, 0.89 mmol) and azobisisobutyronitrile AIBN (30 mg, 0.18 mmol), each dissolved in MeOH (5 ml and 1 ml, respectively) were added. The suspension was stirred under reflux for 6 h. After cooling and filtration, the silica gel was washed with MeOH (3×20 ml), diethylether (2×20 ml), and dried in vacuo at 60° C. to yield the new CSP. SO coverages were calculated from the nitrogen content obtained by elemental analysis: CSP 1 (based on SO 3): w-% C 10.60, w-% H 1.85, w-% N 0.825, w-% S 2.56; 196 µmol SO per g CSP. CSP 2 (based on SO 4): w-% C 10.48, w-% H 1.85, w-% N 0.863, w-% S 3.26; 205 µmol SO per g CSP. CSP 3 (based on SO 5): w-% C 11.53, w-% H 1.96, w-% N 0.905, w-% S 3.19; 215 µmol SO per g CSP. CSP 4 (based on SO 6): w-% C 11.83, w-% H 1.92, w-% N 0.961, w-% S 3.19; 229 µmol SO per g CSP. CSP 5 (based on SO 7): w-% C 10.14, w-% H 1.78, w-% N 0.881, w-% S 3.15; 210 µmol SO per g CSP. CSP 1-5 were slurry packed into stainless steel columns (150×4 mm I.D.) either in house or at VDS Optilab GmbH (Berlin, Germany).

Results and Discussion

Selector Design

The present invention targets a dedicated development of ion exchanger type chiral stationary phases that address both positively and negatively charged chiral analytes. Thereby, the aim was to fuse acidic and basic selector units that have already been employed by us previously as successful low molecular mass SOs in cation and anion exchanger type enantioselective chromatography into novel zwitterionic selector structures. The sulfonic acid based SCX CSP shown in FIG. 1 has been reported for the enantioseparation of various chiral amines in HPLC. Its chiral part is represented by the trans-2-aminocyclohexanesulfonic acid and was therefore selected as cation exchanger site for a zwitterionic CSP. The quinine tert-butyl carbamate derivative WAX (see FIG. 1) is also well established as chiral anion exchanger CSP. Thorough investigations that have been reported on cinchona type receptors in enantioseparation techniques suggested the O9-position of quinine for introducing the aminosulfonic acid via carbamate linkage if enantioselective properties should remain largely unaltered. Novel zwitterionic CSPs in FIG. 2 illustrate the concept of fusing cation and anion exchanger moieties in one single selector where CSP 3 and 4 incorporate key motifs of the WAX- and SCX congeners with the alkaloid base and the cyclohexanesulfonic acid. For more detailed investigations of enantioselective ionic interaction processes also achiral carboxylic and sulfonic acids with amino groups in 3-position were incorporated in CSP 1, 2, and 5. Also in CSP 5, the alkaloid base quinine was replaced by its pseudoenantiomer quinidine which was expected to affect elution order upon enantioseparation and thereby shed more light on the underlying molecular recognition process.

Preparation of CSP 1-5

For carbamate-type derivatization with aminoacids at the O9-position, quinine 1a and quinidine 1b, respectively, were activated by reaction with 4-nitrochloroformate [39] whereupon hydrochloride salts 2a and 2b precipitated from the reaction solution and could be collected by filtration (FIG. 3). The achiral β-aminoacids to be coupled were commercially available compounds like taurine and β-alanine while the chiral trans-2-aminocyclohexanesulfonic acid building block was prepared as a racemate according to published procedures [13,37].

In order to circumvent solubility problems, the different aminoacids where converted into their trimethylsilyl esters with N,O-bis(trimethylsilyl)acetamide [40] prior to reacting with nitrophenylesters 2a and 2b. Amphoteric SOs 3-7 could thereby be quickly prepared in acceptable to good yields. Immobilization of the SOs onto thiol-modified silica gel was accomplished via radical addition reaction [35] and produced novel CSPs 1-5 with SO loadings of 150-230 µmol per gram CSP. In the case of CSPs 3 and 4, preparative separation of diastereomeric SOs prior to immobilization was necessary in order to guarantee for high purity of SO stereoisomers. While both standard reversed-phase (RP) and WAX-type chromatography did not allow feasible separations of the ampholytic compounds, the employment of novel CSP 1, the β-alanine-quinine based zwitterionic material, gave a sufficient separation (analytical run: α=2.24, $R_S$=8.9) and a high loading capacity (up to 10 mg of sample injected onto a 150×4 mm column) while using an easily removable mobile phase consisting of 0.14% acetic acid in MeOH (data not shown). Although being a separation of diastereomers it indicates the potential of these novel chiral zwitterionic stationary phases also for the application of preparative separation and purification of ampholytic compounds.

Chromatographic Evaluation of CSPs 1-5

In the following, results of the chromatographic evaluations of CSPs 1-5 in HPLC for enantiomer separations will be presented and discussed: At first towards acidic analyte species, secondly towards basic amine analytes, and finally towards zwitterionic solutes.

Polar organic mobile phase conditions were selected for these investigations since they have been successfully and extensively used for the parent, purely anionic or cationic ion exchanger CSPs [13,41]. Polar organic mode employs polar organic bulk solvents like methanol and acetonitrile while acidic and basic additives act as co- and counterions and modulate the ionic interactions between charged SO and solutes.

Since the novel zwitterionic separation materials should in the first place illustrate the concept of a more versatile chiral ion exchanger, comparisons of the overall chromatographic performance of zwitterionic CSPs 1-5 with the parent WAX- and SCX CSPs occurred only on a principal level. In this regard, it is referred to the literature where key features of the latter CSP materials have already been reported in great detail [6,13,38].

Enantioseparation of Chiral Acids

In a series of experiments CSPs 1-5 were tested regarding enantioseparations of different chiral acids in order to assess whether the main property of the cinchona-type WAX CSPs—namely enantioseparation of chiral acidic analytes like N-protected aminoacids—could be conserved in the novel zwitterionic CSPs. For this purpose, a small but representative set of eight analytes was compiled that contains N-blocked aminoacids with aromatic, aliphatic, and charged side chains and employs commonly used N-protecting or derivatizating groups. Both the structures of the analytes as well as chromatographic results are listed in Table 1.

TABLE 1

(HPLC enantiomer separation of various chiral acidic analytes on CSP 1-5[a])

| Analyte | | $k_1$ | $\alpha$ | $R_s$ | EO |
|---|---|---|---|---|---|
| NAc-Phe 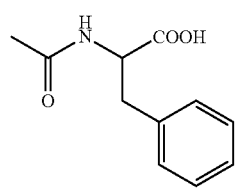 | CSP 1 | 1.04 | 1.43 | 3.75 | D |
| | CSP 2 | 0.29 | 1.50 | 1.80 | D |
| | CSP 3 | 0.24 | 1.62 | 2.29 | D |
| | CSP 4 | 0.41 | 1.40 | 1.88 | D |
| | CSP 5 | 0.18 | 1.54 | 1.58 | L |
| Z-Phe 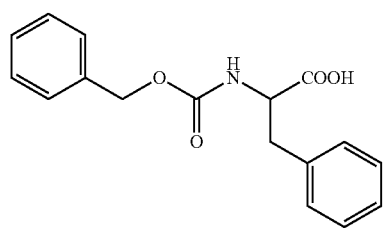 | CSP 1 | 1.92 | 1.19 | 2.15 | D |
| | CSP 2 | 0.63 | 1.17 | 0.78 | D |
| | CSP 3 | 0.55 | 1.24 | 1.63 | D |
| | CSP 4 | 0.95 | 1.13 | 1.12 | D |
| | CSP 5 | 0.36 | 1.21 | 0.98 | L |
| Fmoc-Phe 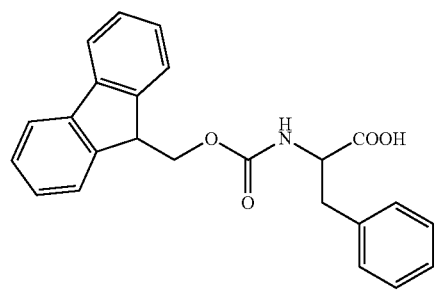 | CSP 1 | 2.95 | 1.37 | 4.05 | D |
| | CSP 2 | 1.03 | 1.35 | 1.80 | D |
| | CSP 3 | 0.94 | 1.52 | 3.35 | D |
| | CSP 4 | 1.51 | 1.27 | 2.30 | D |
| | CSP 5 | 0.59 | 1.33 | 1.68 | L |
| DNB-Phe 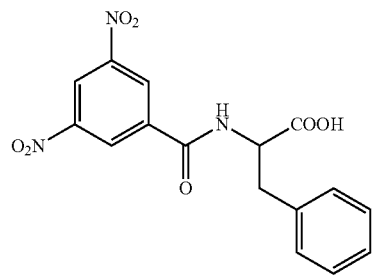 | CSP 1 | 3.18 | 6.38 | 21.93 | D |
| | CSP 2 | 1.01 | 7.22 | 10.92 | D |
| | CSP 3 | 0.97 | 15.03 | 22.43 | D |
| | CSP 4 | 0.43 | 5.00 | 17.55 | D |
| | CSP 5 | 0.58 | 5.61 | 16.16 | L |

TABLE 1-continued (HPLC enantiomer separation of various chiral acidic analytes on CSP 1-5[a])

| Analyte | | $k_1$ | α | $R_s$ | EO |
|---|---|---|---|---|---|
| NAc-Trp | CSP 1 | 1.72 | 1.83 | 7.24 | D |
| 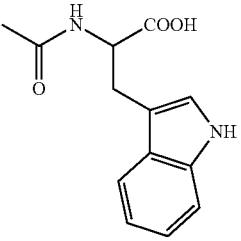 | CSP 2 | 0.77 | 1.93 | 4.24 | D |
| | CSP 3 | 0.80 | 3.01 | 10.74 | D |
| | CSP 4 | 1.00 | 1.54 | 4.25 | D |
| | CSP 5 | 0.36 | 2.10 | 4.78 | L |
| DNP-Phe | CSP 1 | 6.28 | 1.42 | 3.47 | L |
| 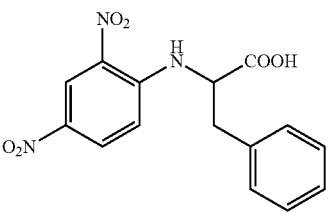 | CSP 2 | 2.13 | 1.53 | 2.94 | L |
| | CSP 3 | 2.06 | 1.48 | 4.63 | L |
| | CSP 4 | 3.48 | 1.77 | 7.77 | L |
| | CSP 5 | 1.22 | 1.30 | 2.91 | D |
| Fmoc-Leu | CSP 1 | 1.34 | 1.33 | 3.10 | n.d. |
| 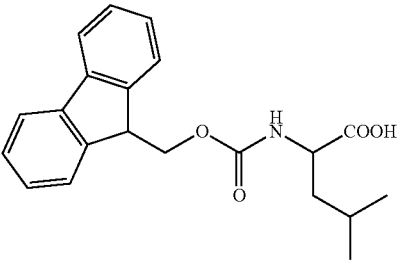 | CSP 2 | 0.47 | 1.27 | 1.12 | n.d. |
| | CSP 3 | 0.43 | 1.43 | 2.35 | n.d. |
| | CSP 4 | 0.67 | 1.32 | 2.25 | n.d. |
| | CSP 5 | 0.31 | 1.22 | 0.96 | n.d. |
| DNB-Glu | CSP 1 | 6.53 | 3.96 | 16.37 | n.d. |
| 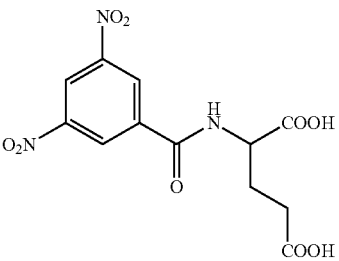 | CSP 2 | 1.54 | 4.40 | 8.91 | n.d. |
| | CSP 3 | 1.48 | 5.82 | 17.71 | n.d. |
| | CSP 4 | 2.16 | 3.08 | 13.14 | n.d. |
| | CSP 5 | 0.69 | 3.62 | 12.09 | n.d. |

[a]Conditions: stationary phase: column dimension 150 × 4 mm I.D.; mobile phase: 50 mM formic acid and 25 mM diethylamine in MeOH; flow 1.0 ml/min; T 25° C.; $t_0$ = 1.49 min. EO = elution order (configuration of the first eluted enantiomer). n.d. = not determined.
$k_1$ = retention factor of first eluted enantiomer; α = separation factor i.e. chromatographic enantioselectivity; $R_s$ = resolution between first and second eluted enatiomers; EO = elution order (configuration of the first eluted enantiomer).

Clearly, enantioselective properties that allow the separation of acidic analyte enantiomers are still present in all five zwitterionic CSPs. With only a few exceptions, all analytes were base-line separated on all CSPs. In comparison to a typical chiral WAX CSP (see FIG. 1) the overall α-values are corroborated with slight variances (data not shown). The effect of the type of protecting group on chiral recognition and enantioselectivity on cinchona-type CSPs has previously been described in detail [35,38] and can be confirmed also with CSPs 1-5: the 3,5-dinitrobenzoyl amides truly yield excellent enantioseparations (α-values up to 15 with resolutions >20), the Fmoc-, DNP- and the acetyl groups give good separations followed by the Z-group; The DNP-group leads to a reversal of the elution order compared the other N-protected groups.

SOs of CSP 1 and CSP 2 are structural homologues which differ only in the type of their acid function. Additionally, both CSPs have almost identical SO loadings. The marked difference in retention between CSP 1 and CSP 2 can therefore be explained with acid strength: The stronger sulfonic acid in CSP 2 is a more dominant—in this particular case intramolecular—counterion compared to the weaker carboxylic acid in CSP 1, and consequently leads to shorter retention times at similar acid concentrations in the mobile phase. Hence, retention factors on carboxylic acid based CSP 1 are up to four fold higher, e.g. as for diacidic DNB-Glu, than on sulfonic acid based CSP 2. At this point it should be noted that the effect of an intrinsic or intramolecular counterion on ionexchanger-based enantioselective chromatography will be the topic of another detailed study that is currently in preparation. The in parts significant differences in enantioselectivity and retention between sulfonic acid type CSPs 3 and 4 at similar SO loadings reflect varying molecular recognition processes of the analytes by their diastereomeric SO.

Elution order of the analyte enantiomers and the ability to switch elution order can be critical, for instance when it comes to impurity profiling and preparative enantioseparation [42]. In this context synthetic low molecular weight SOs and corresponding CSPs can offer the advantage that they allow a switch of elution order by switching to the CSP of opposite configuration. For both parent CSPs of the herein presented zwitterionic CSPs (see FIG. 1) this kind of elution order reversal has been shown previously [13,35,38], e.g. for the quinine-based weak anion exchanger CSP and its pseudoenantiomeric quinidine-based CSP. CSPs 1-5 show similar behavior (Table 1). The elution order of chiral acidic analytes upon enantioseparation is always the same on zwitterionic CSPs 1-4, which are all quinine-based, and matches the in the literature reported elution order of the standard, purely anion exchanger type quinine-based CSP. By contrast, CSP 5, which employs pseudoenantiomeric quinidine as part of the SO, leads to a reversal of the elution order compared to CSPs 1-4. These findings strongly suggest that the novel zwitterionic CSPs exhibit a cinchona base dominated chiral recognition mechanism towards acidic analytes which is very similar to the conventional quinine- and quinidine-type CSP. Consequently, the acidic groups that have been introduced at the O9-position of the alkaloid moiety do not fundamentally alter this molecular recognition scenario.

Enantioseparation of Chiral Amines

After confirmation of enantioselectivity towards chiral acidic analytes due to their cinchona base motif the zwitterionic CSPs were investigated regarding their separation potential towards chiral amine enantiomers on the basis of their cation exchanger site. It was particularly interesting to assess if enantioselectivity could be transferred by incorporation of the trans-2-aminocyclohexanesulfonic acid moiety from the SCX CSP into the novel ampholytic SOs or if even an achiral acidic side chain in conjunction with the alkaloid structure could provide enantioselectivity for chiral amine solutes. For that purpose, a set of 12 chiral bases was studied which contained largely pharmaceuticals such as β-blockers, β-sympathomimetics, and other drugs (see Table 2). Chromatography was carried out using nonoptimized mobile phase conditions which were directly adopted from the recently reported study on SCX CSPs [13]. The results are summarized in Table 2.

TABLE 2

(HPLC enantiomer separation of various chiral basic analytes on CSP 1-5[a])

| Analyte [b] | | $k_1'$ | α | $R_s$ | EO |
|---|---|---|---|---|---|
| 1,1-Diphenylprolinol 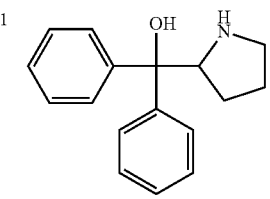 | CSP 1 | 1.24 | 1.00 | 0.00 | |
| | CSP 2 | 2.91 | 1.00 | 0.00 | |
| | CSP 3 | 2.89 | 1.18 | 2.77 | −/+ |
| | CSP 4 | 3.20 | 1.08 | 1.26 | +/− |
| | CSP 5 | 1.54 | 1.00 | 0.00 | |
| Bamethan 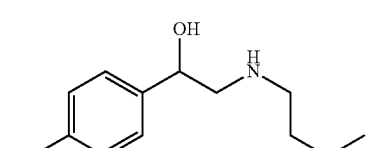 | CSP 1 | 2.21 | 1.00 | 0.00 | |
| | CSP 2 | 6.20 | 1.00 | 0.00 | |
| | CSP 3 | 6.51 | 1.17 | 2.93 | −/+ |
| | CSP 4 | 5.60 | 1.00 | 0.00 | |
| | CSP 5 | 2.52 | 1.00 | 0.00 | |
| Butoxamine 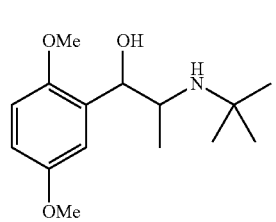 [SMILES: COc1ccc(OC)c(C(O)C(C)NC(C)(C)C)c1] | CSP 1 | 0.83 | 1.13 | 0.56 | +/− |
| | CSP 2 | 1.94 | 1.12 | 1.57 | +/− |
| | CSP 3 | 1.59 | 1.17 | 2.34 | −/+ |
| | CSP 4 | 1.69 | 1.15 | 2.24 | +/− |
| | CSP 5 | 1.07 | 1.11 | 1.30 | −/+ |

TABLE 2-continued (HPLC enantiomer separation of various chiral basic analytes on CSP 1-5[a])

| Analyte [b] | | $k_1'$ | α | $R_s$ | EO |
|---|---|---|---|---|---|
| Mefloquine [c), d)] | CSP 1 | 1.06 | 1.86 | 1.49 | +/− |
| | CSP 2 | 1.97 | 1.31 | 3.28 | +/− |
| 4 | CSP 3 | 1.17 | 15.17 | 11.97 | +/− |
| | CSP 4 | 1.89 | 1.63 | 3.80 | +/− |
| | CSP 5 | 0.79 | 1.74 | 5.16 | −/+ |
| Pseudo-Ephedrine | CSP 1 | 1.02 | 1.00 | 0.00 | |
| | CSP 2 | 3.14 | 1.00 | 0.00 | |
| 5 | CSP 3 | 2.83 | 1.16 | 2.38 | −/+ |
| | CSP 4 | 2.40 | 1.00 | 0.00 | |
| | CSP 5 | 1.59 | 1.00 | 0.00 | |
| Lorazepam [c)] | CSP 1 | 0.44 | 1.00 | 0.00 | |
| | CSP 2 | 0.51 | 1.00 | 0.00 | |
| 6 | CSP 3 | 0.46 | 1.32 | 2.09 | n.d. |
| | CSP 4 | 0.38 | 1.10 | 0.59 | n.d. |
| | CSP 5 | 0.36 | 1.12 | 0.63 | n.d. |
| Flecainid | CSP 1 | 0.65 | 1.00 | 0.00 | |
| | CSP 2 | 2.03 | 1.00 | 0.00 | |
| 7 | CSP 3 | 2.21 | 1.15 | 2.06 | +/− |
| | CSP 4 | 1.93 | 1.16 | 2.22 | −/+ |
| | CSP 5 | 1.05 | 1.00 | 0.00 | |
| Isoxsuprine | CSP 1 | 1.51 | 1.00 | 0.00 | |
| | CSP 2 | 3.49 | 1.03 | 0.20 | +/− |
| 8 | CSP 3 | 3.68 | 1.18 | 2.81 | −/+ |
| | CSP 4 | 3.43 | 1.25 | 3.74 | +/− |
| | CSP 5 | 1.47 | 1.00 | 0.00 | |

TABLE 2-continued (HPLC enantiomer separation of various chiral basic analytes on CSP 1-5[a])

| Analyte [b] | | $k_1'$ | α | $R_s$ | EO |
|---|---|---|---|---|---|
| O-tBu-carbamoyl-Mefloquine [d] | CSP 1 | 0.83 | 1.00 | 0.00 | |
| 9 | CSP 2 | 2.04 | 1.09 | 1.08 | +/− |
| | CSP 3 | 2.27 | 1.16 | 2.11 | −/+ |
| | CSP 4 | 2.00 | 2.55 | 12.8 | +/− |
| | CSP 5 | 1.07 | 1.00 | 0.00 | |
| Isopenbutolol | CSP 1 | 0.83 | 1.00 | 0.00 | |
| 10 | CSP 2 | 2.37 | 1.04 | 0.54 | +/− R/S |
| | CSP 3 | 2.21 | 1.20 | 2.87 | +/− R/S |
| | CSP 4 | 2.10 | 1.05 | 0.67 | +/− R/S |
| | CSP 5 | 1.27 | 1.00 | 0.00 | |
| Bunitrolol | CSP 1 | 0.87 | 1.00 | 0.00 | |
| 11 | CSP 2 | 2.16 | 1.06 | 0.58 | +/− |
| | CSP 3 | 1.85 | 1.18 | 2.51 | +/− |
| | CSP 4 | 1.79 | 1.04 | 0.56 | +/− |
| | CSP 5 | 1.15 | 1.00 | 0.00 | |
| Celiprolol | CSP 1 | 0.99 | 1.00 | 0.00 | |
| 12 | CSP 2 | 2.71 | 1.05 | 0.56 | R/S |
| | CSP 3 | 2.13 | 1.21 | 2.81 | R/S |
| | CSP 4 | 2.03 | 1.04 | 0.56 | R/S |
| | CSP 5 | 1.21 | 1.00 | 0.00 | |

[a] Conditions: column dimension 150 x 4 mm I.D.; mobile phase: 50 mM formic acid and 25 mM diethylamine in acetonitrile/MeOH (9/1, v/v); flow 1.0 ml/min; T 25° C.; $t_0$ = 1.49 min. UV detection at 254 nm. n.d. = not determined. EO = elution order (ORD detection).
[b] Analyte description: name, entry number, structural forumula
[c] Mobile phase: 50 mM formic acid and 25 mM diethylamine in MeOH
[d] Mefloquine: erythro-alpha-2-piperidinyl-2,8-bis(trifluoromethyl)-4-quinolinemethanol Overall, there are two distinct observations which correlate with the chirality of the acidic selector subunit. Both zwitterionic CSPs 3 and 4—that have chiral acidic moieties—show enantioselectivity towards the selected analytes similar to the parent SCX CSP in the range of α=1.05-2.00. Thereby, CSP 3 clearly provides a broad application range by base-line separating all of the 12 analytes. CSP 4 however shows less pronounced enantioselectivity by separating only one analyte better than CSP 3 (entry 8 in Table 2) and five solutes in total. In contrast, CSPs 1, 2, and 5—each with acidic but achiral side chains—show negligible enantioselectivity towards the chosen set of analytes, with the exception of the anti-malarial drug Mefloquine (entry 4) which can be base-line separated with any of the five zwitterionic CSPs. This leads to the conclusion that the chiral trans-2-aminocyclohexanesulfonic acid moiety in CSP 3 and 4 is truly beneficial but not essential for the observed enantioselective properties of the discussed zwitterionic CSPs towards chiral amines. The measured elution orders do not show a general trend.

When operating CSP 3 and 4, which rely on diastereomeric chiral selectors but with opposite configuration in their acid subunits, reversal of elution order was found for five solutes (entries 1, 3, 7, 8, and 9) while for four other analytes elution order remained unchanged (entries 4, 10, 11, and 12) which is a clear indication that the chiral subunits of the fused zwitterionic entity do not act entirely independently from each other. Furthermore, comparison of elution orders on pseudoenantiomeric CSPs 2 and 5 (entries 3 and 4) points towards a guiding influence of the alkaloid motif. Obviously, it seems as if besides the crucial role of the chiral β-aminocyclohexanesulfonic acid moieties also the "chiral environment" of the alkaloid substructure is to some extend involved in an overall chiral recognition process towards the herein selected amine analytes. For instance, the very high enantioselectivity for Mefloquine (α>15 on CSP 3) suggests that in this specific case the quinine motif is crucial and, in combination with the chiral acid subunit, enables an almost "ideal fit" of the well bound Mefloquine enantiomer which results also in a strong increase of its retention.

The above-mentioned results on enantioseparations of chiral acids and chiral amines truly state that the concept of combining of both anion and cation exchanger in one SO motif has succeeded, especially with CSPs 3 and 4 where the chiral acidic and basic subunits that have been selected still work as proven when fused together in one single selector. Consequently, novel zwitterionic materials like CSP 3 and 4 now allow enantiomer separations of chiral acids and chiral bases with one single but zwitterionic ion exchanger type CSP.

Enantioseparation of Chiral Zwitterionic Analytes

Direct chromatographic enantiomer separations of zwitterionic analytes like unprotected amino acids by means of CSPs based on zwitterionic SOs could open up new applications for enantioselective ion exchangers. Therefore, it was first of all crucial to determine if this phenomenon could be of broad scope, and whether or not we could gain insights into this expanded interaction mechanism of chiral zwitterionic ion exchangers. For these purposes, a rather large, divers set of zwitterionic analytes was compiled (Table 3) which included cyclic and acyclic, natural and nonnatural α- and β-aminoacids with one and two chiral centers, with primary and secondary amino groups, with carboxylic and sulfonic acids, and with aliphatic, aromatic and functional group containing side chains as well as several dipeptides.

TABLE 3

(HPLC enantiomer separation of various chiral zwitterionic analytes on CSP 1-5[a])

| Analyte [b] | | $k_1'$ | α | $R_s$ | EO |
|---|---|---|---|---|---|
| Leucine | | | | | |
| 1 H₂N─COOH | CSP 3 | 1.07 | 1.23 | 1.57 | |
| | CSP 4 | 0.60 | 1.00 | 0.00 | |
| Isoleucine | | | | | |
| 2 H₂N─COOH | CSP 3 | 1.00 | 1.26 | 1.77 | |
| | CSP 4 | 0.56 | 1.14 | 0.62 | |
| Norleucine | | | | | |
| 3 H₂N─COOH | CSP 3 | 1.01 | 1.26 | 1.80 | |
| | CSP 4 | 0.61 | 1.05 | 0.35 | |
| Neopentylglycine | | | | | |
| 4 H₂N─COOH | CSP 3 | 1.21 | 1.38 | 3.04 | |
| | CSP 4 | 0.67 | 1.14 | 0.80 | |
| Phenylglycine | | | | | |
| | CSP 1 | 0.52 | 1.00 | 0.00 | — |
| | CSP 2 | 0.87 | 1.00 | 0.00 | — |
| 5 H₂N─COOH | CSP 3 | 1.47 | 1.03 | 0.37 | L |
| | CSP 4 | 0.73 | 1.17 | 1.22 | D |
| | CSP 5 | 0.45 | 1.13 | 0.66 | D |

TABLE 3-continued (HPLC enantiomer separation of various chiral zwitterionic analytes on CSP 1-5[a])

| Analyte [b] | | $k_1'$ | α | $R_s$ | EO |
|---|---|---|---|---|---|
| β-Phenylalanine 6 | CSP 1 | 0.63 | 1.00 | 0.00 | — |
| | CSP 2 | 1.46 | 1.01 | 0.15 | S |
| | CSP 3 | 3.92 | 1.11 | 1.45 | S |
| | CSP 4 | 1.05 | 1.16 | 1.41 | S |
| | CSP 5 | 0.85 | 1.09 | 0.67 | R |
| Threonine 7 | CSP 3 | 1.34 | 1.24 | 1.80 | |
| | CSP 4 | 0.69 | 1.00 | 0.00 | |
| Eflornithine 8 | CSP 3 | 8.88 | 1.31 | 1.14 | |
| | CSP 4 | 2.53 | 1.36 | 1.10 | |
| α-Methyl-Leucine 9 | CSP 3 | 0.62 | 1.00 | 0.00 | |
| | CSP 4 | 0.33 | 1.47 | 1.67 | |
| Allo-Isoleucine 10 | CSP 3 | 0.99 | 1.28 | 1.86 | |
| | CSP 4 | 0.55 | 1.11 | 0.56 | |
| tBu-Glycine 11 | CSP 3 | 0.92 | 1.45 | 3.06 | |
| | CSP 4 | 0.54 | 1.08 | 0.50 | |
| β-Neopentylglycine 12 | CSP 3 | 2.18 | 1.31 | 2.84 | |
| | CSP 4 | 0.57 | 1.00 | 0.00 | |

TABLE 3-continued
(HPLC enantiomer separation of various chiral zwitterionic analytes on CSP 1-5[a])
| Analyte [b] | | $k_1'$ | α | $R_s$ | EO |
|---|---|---|---|---|---|
| Phenylalanine | CSP 1 | 0.51 | 1.00 | 0.00 | — |
| | CSP 2 | 0.77 | 1.06 | 0.45 | D |
| 13 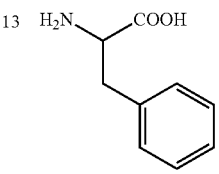 | CSP 3 | 1.16 | 1.17 | 1.50 | L |
| | CSP 4 | 0.73 | 1.00 | 0.00 | — |
| | CSP 5 | 0.46 | 1.00 | 0.00 | — |
| α-Methyl-Phe | CSP 1 | 0.39 | 1.29 | 0.75 | D |
| | CSP 2 | 0.65 | 1.28 | 1.99 | D |
| 14 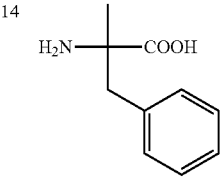 | CSP 3 | 0.75 | 1.17 | 1.38 | D |
| | CSP 4 | 0.60 | 1.44 | 2.72 | D |
| | CSP 5 | 0.38 | 1.25 | 1.38 | L |
| Glutamate | | | | | |
| 15 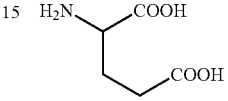 | CSP 3 | 2.28 | 1.25 | 2.20 | D |
| | CSP 4 | 1.25 | 1.03 | 0.33 | n.d. |
| Cysteic acid | | | | | |
| 16 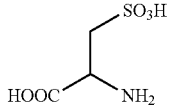 | CSP 3 | 4.35 | 1.15 | 1.09 | |
| | CSP 4 | 1.84 | 1.07 | 0.53 | |
| Gly-Phe | | | | | |
| 17 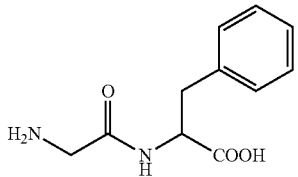 [SMILES: NCC(=O)NC(Cc1ccccc1)C(=O)O] | CSP 3 | 2.77 | 1.00 | 0.00 | — |
| | CSP 4 | 1.42 | 1.29 | 2.60 | n.d. |
| Tyrosine | CSP 1 | 0.64 | 1.08 | 0.19 | D |
| | CSP 2 | 1.06 | 1.07 | 0.38 | n.d. |
| 18 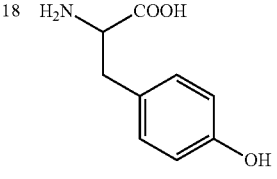 | CSP 3 | 1.65 | 1.10 | 0.79 | n.d. |
| | CSP 4 | 0.97 | 1.00 | 0.00 | — |
| | CSP 5 | 0.53 | 1.04 | 0.26 | n.d. |
| m-Tyrosine | | | | | |
| 19 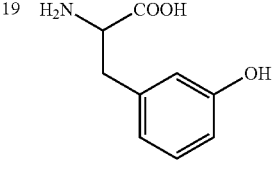 | CSP 3 | 1.17 | 1.08 | 1.65 | |
| | CSP 4 | 1.14 | 1.07 | 0.62 | |

TABLE 3-continued (HPLC enantiomer separation of various chiral zwitterionic analytes on CSP 1-5[a])

| Analyte [b] | | $k_1'$ | α | $R_s$ | EO |
|---|---|---|---|---|---|
| DOPA 20 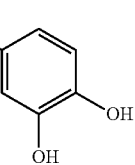 | CSP 3<br>CSP 4 | 2.26<br>1.26 | 1.07<br>1.12 | 0.51<br>0.68 | |
| Acetidine carboxylic acid 21 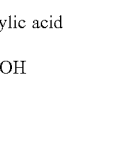 | CSP 3<br>CSP 4 | 1.35<br>1.07 | 1.34<br>1.00 | 2.58<br>0.00 | |
| 3,4-Dehydroproline 22  | CSP 3<br>CSP 4 | 1.05<br>0.67 | 1.89<br>1.29 | 5.00<br>1.30 | |
| Pipecolinic acid 23  | CSP 3 | 0.90 | 1.12 | 0.87 | |
| Nipecotic acid 24  | CSP 3<br>CSP 4 | 2.32<br>1.42 | 1.92<br>1.25 | 5.95<br>1.71 | |
| Ala-Phe (D,D)/(L,L) 25 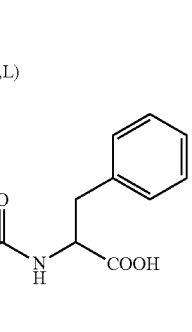 | CSP 3<br>CSP 4 | 1.57<br>1.19 | 1.33<br>1.68 | 2.85<br>5.44 | n.d.<br>n.d. |
| α-Methyl-Tyrosine 26 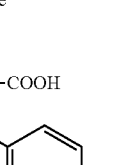 | CSP 1<br>CSP 2<br>CSP 3<br>CSP 4<br>CSP 5 | 0.46<br>0.61<br>0.97<br>0.74<br>0.44 | 1.35<br>1.37<br>1.21<br>1.44<br>1.30 | 0.87<br>2.63<br>1.76<br>2.89<br>1.67 | D<br>D<br>D<br>D<br>L |

TABLE 3-continued (HPLC enantiomer separation of various chiral zwitterionic analytes on CSP 1-5[a])

| Analyte [b] | | $k_1'$ | α | $R_s$ | EO |
|---|---|---|---|---|---|
| α-Methyl-m-Tyr 27 | CSP 1 | 0.53 | 1.43 | 1.24 | n.d. |
| | CSP 2 | 0.82 | 1.34 | 1.72 | n.d. |
| | CSP 3 | 1.00 | 1.48 | 3.90 | n.d. |
| | CSP 4 | 0.87 | 1.50 | 3.58 | n.d. |
| | CSP 5 | 0.47 | 1.41 | 2.41 | n.d. |
| α-Methyl-DOPA 28 | CSP 1 | 0.74 | 1.46 | 0.44 | D |
| | CSP 2 | 1.15 | 1.49 | 3.57 | D |
| | CSP 3 | 1.35 | 1.51 | 3.83 | D |
| | CSP 4 | 1.06 | 1.54 | 3.48 | D |
| | CSP 5 | 0.55 | 1.40 | 2.45 | L |
| Proline 29 | CSP 3 | 1.12 | 1.59 | 3.80 | |
| | CSP 4 | 0.69 | 1.21 | 1.06 | |
| α-Methyl-Proline 30 | CSP 3 | 0.71 | 1.71 | 4.47 | |
| | CSP 4 | 0.55 | 1.14 | 0.82 | |
| α-Benzyl-Proline 31 | CSP 3 | 0.66 | 1.74 | 3.89 | |
| | CSP 4 | 0.70 | 1.94 | 4.56 | |
| Tic [c] 32 | CSP 1 | 0.52 | 1.00 | 0.00 | — |
| | CSP 2 | 0.84 | 1.10 | 0.78 | S |
| | CSP 3 | 1.21 | 1.33 | 3.07 | S |
| | CSP 4 | 0.84 | 1.15 | 1.11 | S |
| | CSP 5 | 0.53 | 1.10 | 0.69 | R |
| CHSA [d] 33 | CSP 3 | 3.59 | 1.07 | 0.84 | |
| | CSP 4 | 0.90 | 1.00 | 0.00 | |

TABLE 3-continued (HPLC enantiomer separation of various chiral zwitterionic analytes on CSP 1-5[a])

| Analyte [b] | | $k_1'$ | α | $R_s$ | EO |
|---|---|---|---|---|---|
| 2-Pyrrolidinemethane-sulfonic acid | | | | | |
| 34 | CSP 3 | 2.21 | 1.22 | 2.59 | |
|    | CSP 4 | 0.77 | 1.20 | 1.49 | |
| Tryptophane | CSP 1 | 0.79 | 1.49 | 1.02 | D |
|             | CSP 2 | 1.50 | 1.61 | 5.13 | D |
| 35          | CSP 3 | 2.48 | 1.66 | 6.12 | D |
|             | CSP 4 | 1.48 | 1.52 | 4.11 | D |
|             | CSP 5 | 0.77 | 1.44 | 3.29 | L |
| erythro-β-Methyl-Trp | | | | | |
| 36 | CSP 2 | 1.23 | 2.15 | 9.26 | |
|    | CSP 3 | 2.87 | 2.25 | 9.98 | |
|    | CSP 4 | 1.54 | 1.93 | 7.26 | |
| 1,2-Dimethyl Taurine (S,R)/(R,S) | | | | | |
| 37 | CSP 3 | 0.85 | 1.75 | 5.36 | |
|    | CSP 4 | 0.44 | 1.14 | 0.67 | |
| 2-Amino-3,3-dimethyl-1-butanesulfonic acid | | | | | |
| 38 | CSP 3 | 1.42 | 2.51 | 10.12 | D |
|    | CSP 4 | 0.53 | 1.10 | 0.58  | D |
| α-Methyl-Trp | CSP 1 | 0.73 | 2.34 | 3.73 | n.d. |
|              | CSP 2 | 1.40 | 2.66 | 11.41 | n.d. |
| 39           | CSP 3 | 1.70 | 3.69 | 15.38 | n.d. |
|              | CSP 4 | 1.39 | 2.61 | 10.28 | n.d. |
|              | CSP 5 | 0.73 | 2.42 | 8.66  | n.d. |

TABLE 3-continued (HPLC enantiomer separation of various chiral zwitterionic analytes on CSP 1-5[a])

| Analyte [b] | | $k_1'$ | $\alpha$ | $R_s$ | EO |
|---|---|---|---|---|---|
| 1-Methyl-Trp | CSP 1 | 0.85 | 1.29 | 0.64 | D |
|  | CSP 2 | 1.44 | 1.33 | 2.02 | D |
| 40 | CSP 3 | 2.29 | 1.38 | 3.66 | D |
|  | CSP 4 | 1.34 | 1.59 | 4.11 | D |
|  | CSP 5 | 0.81 | 1.21 | 1.70 | L |

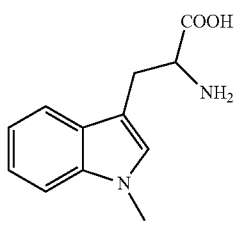 [SMILES: Cn1cc(CC(N)C(=O)O)c2ccccc21]

[a] Conditions: column dimension 150 x 4 mm I.D.; mobile phase: 50 mM formic acid and 25 mM $NH_3$ in MeOH; flow 1.0 ml/min; T 25° C.; $t_0$ = 1.49 min.
[b] Analyte description: name, entry number, structural formula.
[c] Tic: 1,2,3,4-tetrahydroiso-quinoline-3-carboxylic acid
[d] CHSA: trans-2-aminocyclohexanesulfonic acid (1S,2S)/(1R,2R)

Chromatographic conditions that have been applied for the enantioseparations of chiral acids and chiral amines (see sections above) proved to be directly applicable also for enantioseparation of zwitterionic analytes. Therefore and for the benefit of clarity of the concept, no mobile phase optimizations were carried out for the herein presented studies on zwitterionic solutes. However, mobile phase variations are expected to allow an analyte-specific optimization of elution and separation of zwitterionic solutes, especially with regard to pH in aqueous or proton activity in nonaqueous eluent systems.

Chromatographic results and solute structures are both depicted in Table 3, but prior to discussing these results in detail, some additional information should be provided: In a control experiment, both parent types of CSPs (see FIG. 1) were tested for their enantiomer separation capabilites—quinine-based WAX towards basic and zwitterionic solutes, and 2-aminocyclohexanesulfonic acid-based SCX towards acidic and zwitterionic analytes from Tables 1-3. Basic analytes injected onto the WAX type CSP eluted just before the void volume of the column indicating a slight repulsion instead of attraction and were not enantioseparated. Acidic solutes injected onto the SCX type CSP showed similar behavior. These findings can be explained with the fact that if SO and solute both carry a charge of the same sign, dominantly an electrostatic repulsion occurs and the solutes are excluded rather than retained by the CSP. For zwitterionic analytes under the given, weakly acidic mobile phase conditions, only very weak retentions and no enantioseparations were observed on both CSPs (corresponding data not shown)—unlike when employing the novel zwitterionic CSPs. These findings lead to the conclusion that both charged sites of the solute, the protonated amine and the dissociated acid, are recognized quasi simultaneously by the likewise doubly ionized zwitterionic SOs of CSPs 1-5 and that this double ionic interaction is fundamental for the observed enantioseparation of zwitterionic analytes on zwitterionic CSPs 1-5.

For all compounds shown in Table 3, base-line separation or at least partial separation could be achieved with one of the five zwitterionic CSPs. Since the set of analytes is quite divers a broad scope of applicability regarding enantiomer separations of chiral zwitterionic analytes could be assigned for the novel zwitterionic CSPs. Of course column performance is not equally distributed among the different CSPs and towards each of the analytes. Regarding the trends among the analyte structures for instance, the group of tryptophane and its derivatives could be very well separated while for other aminoacids that contain aromatic groups like the phenylalanines and the tyrosines enantioselectivities were lower and separation could not always be reached. Moreover, cyclic aminoacids having a secondary amine group were slightly better separated than acyclic aliphatic aminoacids of the leucine- and glycine-type which might be due to their more rigid structure. Still, it is surprising that no separation occurred for the trans-2-aminocyclohexanesulfonic acid (entry 33), a moiety which is an essential part of the SOs of CSP 3 and 4, while for 1,2-dimethyl taurine (entry 37), the acyclic counterpart, decent enantioselectivity was obtained. A more general observation was that for α-alkyl substituted α-aminoacids enantioselectivity was clearly increased compared to the nonsubstituted compounds as can be seen e.g. for phenylalanine (entries 13 and 14) or tyrosine (entries 18 and 28).

Overall, separation sometimes suffered from peak tailing where despite decent enantioselectivities no base-line separations could be observed, e.g. in the case of eflornithine and other aminoacids that carry additional functional groups. Here, additional charged or partially charged groups and functional groups that can act as H-bond donors or acceptors might interfere with a precisely oriented binding of zwitterionic analyte and SO, and therefore lead to decreased desorption kinetics. Optimal adjustment of the mobile phase and its pH or proton activity is expected to reduce such phenomena but was not further investigated in this study.

The CSPs presented in this work relate either to a weak cation/weak anion exchanger (CSP 1) or to strong cation/weak anion exchangers (CSP 2-5). In this context, a zwitterionic SO that consists of both a strong cation exchanger and a strong anion exchanger moiety, that is, a sulfonic acid like CSPs 2-4 and a quaternized quinuclidine nitrogen, could be very insightful and is currently under investigation by our group.

Besides surveying the data shown in Table 3 in view of analyte structures, also the structural differences of the CSPs' selectors and their consequences for enantioseparation and chromatography have to be considered.

CSP 1 and CSP 2 have been synthesized and tested for the purpose of comparing the carboxylic and sulfonic acid function within a zwitterionic SO. Their SOs are structural homologues but differ only in the type of their acidic function (FIG. 1) and both CSPs have very similar SO loadings which allows their direct comparison. Results from Table 3 indicate marked differences on separation performance for CSP 1 and 2. Retention factors are always smaller on the carboxylic acid based CSP 1 than on the sulfonic acid based CSP 2. Obviously, a stronger acid moiety in the SO leads to a stronger ionic interaction with basic substituents of the zwitterionic analytes under the given mobile phase conditions. Furthermore, CSP 2 provides better peak efficiency which holds with no exception for noticeably improved resolution even if enantioselectivity is similar as can be seen exemplary from entry 28 (Table 3). CSP 1 is most likely susceptible to mobile phase optimization but the sulfonic acid function is clearly better suited for an easy-to-use zwitterionic CSP.

CSPs 3 and 4 both rely on quinine- and trans-2-amino-cyclohexanesulfonic acid-based selectors but are diastereomers due to opposite configurations within the acid part. Despite their principal structural similarity it is therefore expected that they exhibit differences in enantioselectivity upon binding zwitterionic analytes. Supportive for a direct comparison are almost identical SO loadings for both corresponding CSPs 3 and 4. Thus, it is even more surprisingly that CSP 3 shows larger retention factors for all but only one analyte from table 3 (entry 31). Apparently, the steric geometry of CSP 3's zwitterionic binding site allows an overall tighter binding of amino acids and peptides compared to CSP 4. In principle, though, does stronger binding not necessarily mean higher enantioselectivity. However, roughly 75% of all analytes are also better separated on CSP 3 than on CSP 4.

Figure 4:
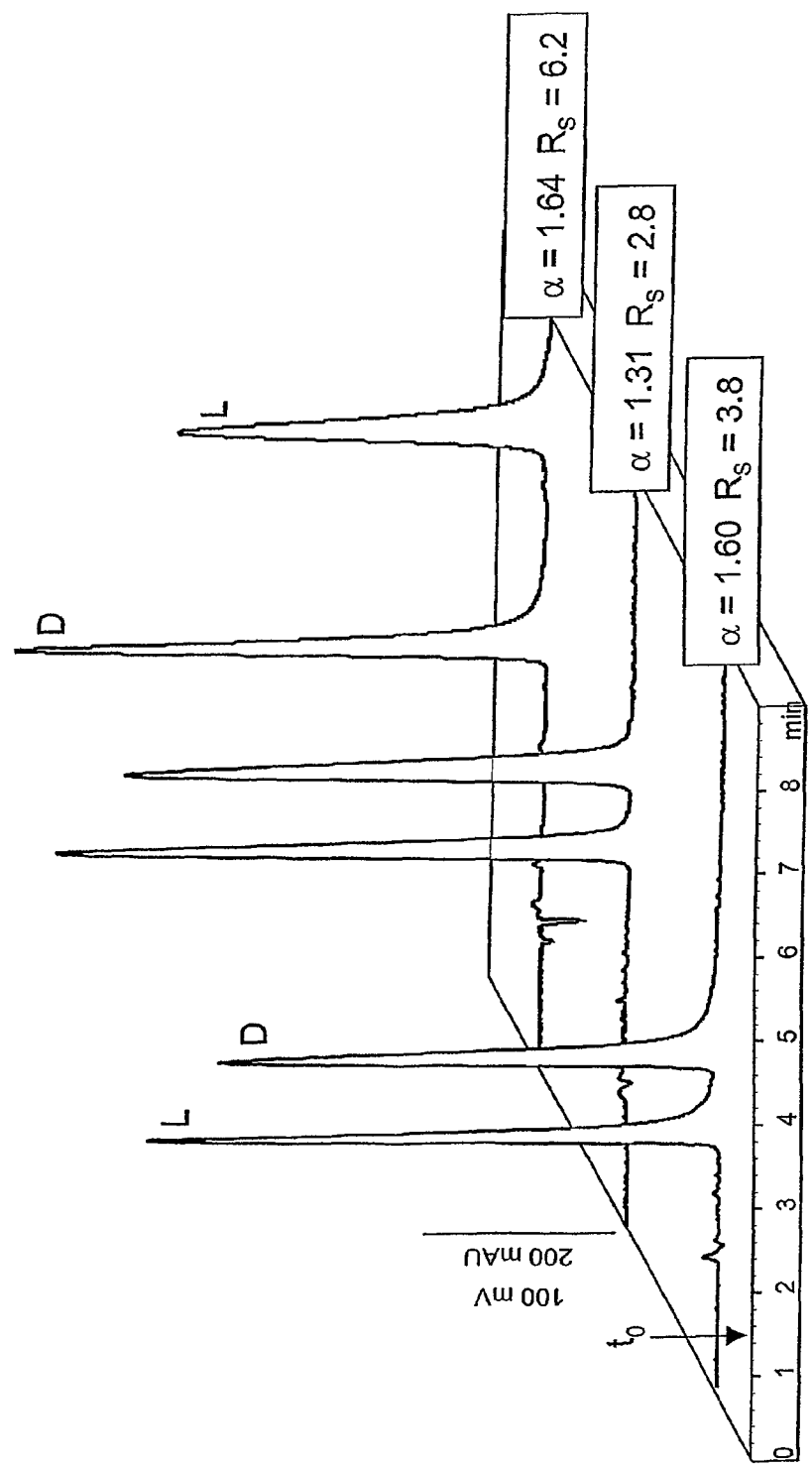
FIG. 4 graphically illustrates selected chromatograms of enantiomer separations of a β-amino acid (β-neopentyl glycine), a cyclic amino acid (proline), and tryptophane using CSP 3.

All in all, CSP 3 provides both most of separations as well as the best separations among all CSPs presented in this study. It therefore exemplifies the potential of synthetically optimized chiral SO structures and could guide further selector design and synthesis. As a supplementary illustration of the above discussed data from table 3, selected chromatograms of enantiomer separations of a β-amino acid (β-neopentyl glycine, entry 12), a cyclic amino acid (proline, entry 29), and tryptophane (entry 35) using CSP 3 are shown in FIG. 4.

Elution order is a necessary information to elucidate the mechanism of chiral recognition and, in the present cases, to attribute enantioselective interactions to the different acidic and basic subunits of the SOs in the series of CSPs 1-5. Therefore, the elution orders of several analytes from Table 3 were determined. At first, the influence of the acid subunit is to be regarded since the acidic moieties of CSP 3 and CSP 4 are of opposite configuration and could potentially influence elution order. As discussed above, CSP 3 and 4 differ in retention and selectivity upon the analysis of zwitterionic solutes, too. Still, no change in elution order towards amphoteric amino acid analytes is observed between the two cyclohexanesulfonic acid based materials, indicating that the chiral acidic moieties are important but not dominant in the zwitterionic enantiodiscriminating process. Furthermore, also CSP 1 and 2, which contain achiral acidic moieties, show identical elution orders like CSP 3 and 4. In other words, all four CSPs that employ the quinine motif provide the same elution order. Only with CSP 5, which is based on quinidine and is pseudoenantiomeric to CSP 2, elution orders of zwitterionic solutes are inverted. These findings strongly suggest that the alkaloid geometry is in the core of the chiral recognition and enantiomer differentiation not only for chiral acidic analytes but also for chiral zwitterionic and ampholytic compounds.

Figure 5:
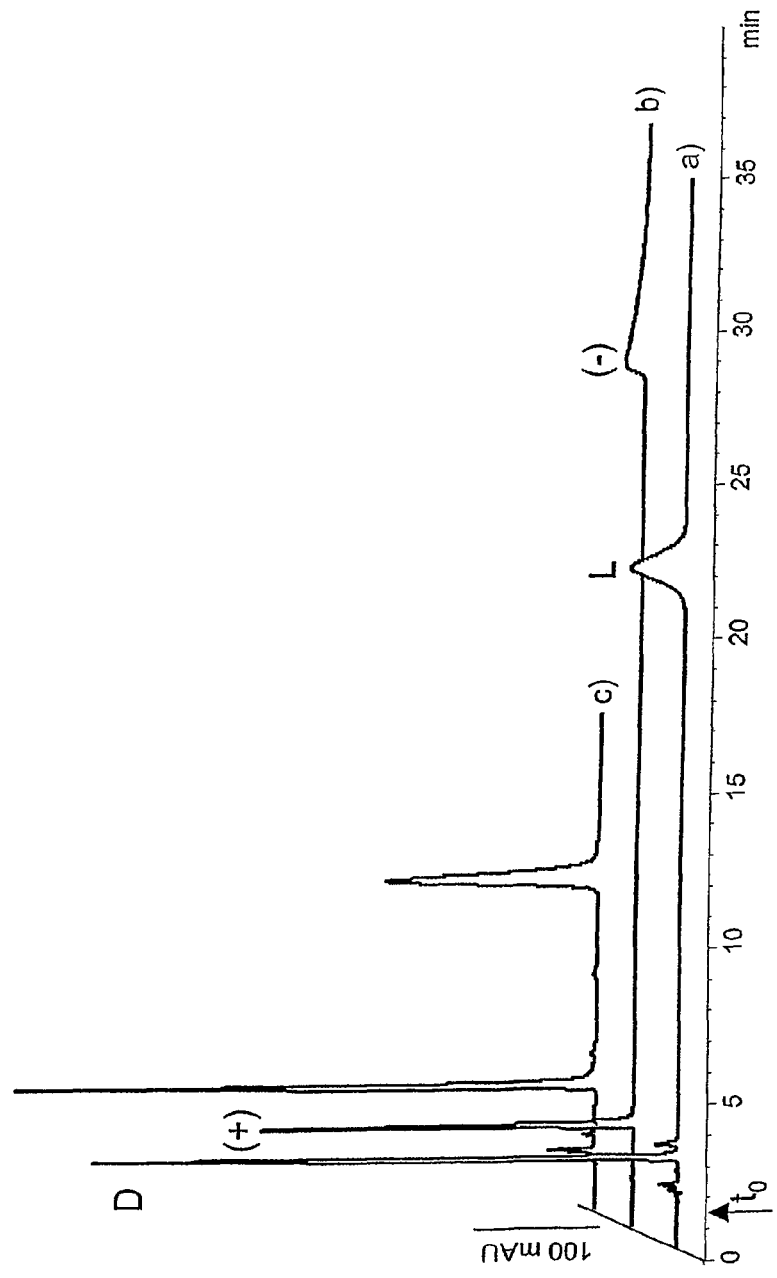
FIG. 5 graphically illustrates selected chromatograms of enantiomer separations of the chiral basic drug Mefloquine, an N-protected phenylalanine, and a free aminoacid obtained with CSP 3.

The novel class of chiral zwitterionic stationary phases presented in this work demonstrate remarkable enantioselective properties of separating not only chiral acids or chiral amines, but both—and additionally zwitterionic compounds as well—through a synergistically supported ion-pairing (ion exchange)-mediated process. FIG. 5 depicts these features with chromatograms of enantiomer separations of the chiral basic drug Mefloquine, an N-protected phenylalanine, and a free aminoacid, obtained with CSP 3.

Figure 1A:
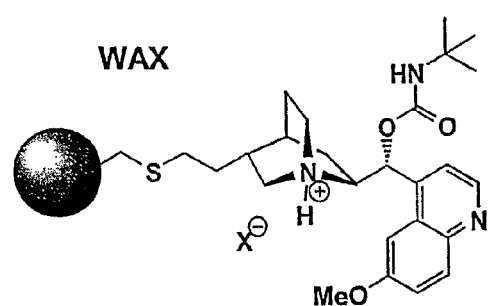
FIG. 1a shows the SO structure of a quinine-type weak anion exchanger (WAX) chiral stationary phase (CSP).
Figure 1B:
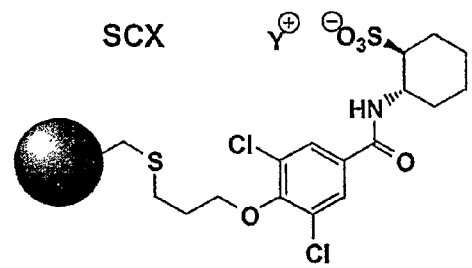
FIG. 1b shows the SO structure of a sulfonic acid based anion exchanger CSP.
Figure 6:
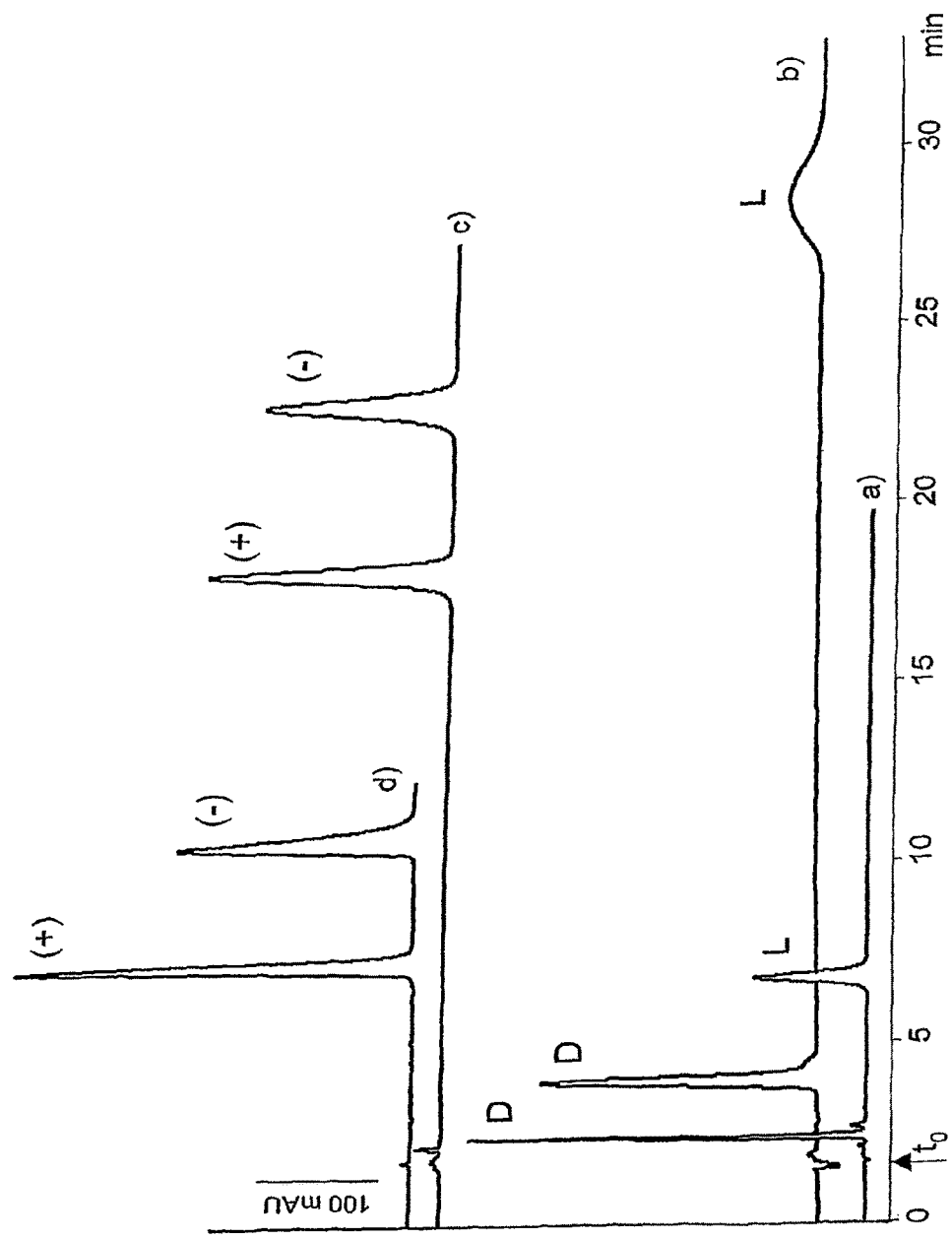
FIG. 6 graphically illustrates a comparison of a novel zwitterionic separation material, CSP 4, and its parent, pure cation and anion exchanger CSPs SCX and QN-AX.

FIG. 6 illustrates a comparison of a novel zwitterionic separation material, CSP 4, and its parent, pure cation and anion exchanger CSPs SCX and QN-AX (see FIG. 1). Obviously, elution behavior has dramatically changed due to the intramolecular counterions present in the chiral selector structure of CSP 4. Enantioselectivity could well be maintained upon fusion of chiral cation and anion exchanger substructures into one single chiral selector.

CONCLUSION

Novel ion exchanger type CSPs based on zwitterionic SOs have been prepared and evaluated for the enantiomer separation of chiral acids, chiral amines, and of chiral amino acids in HPLC.

The inventive SOs resemble a combination of cation- and anion exchanger SO motifs in one single chiral compound. Their synthesis is straightforward using largely conventional and commerically available starting materials. Enantioselectivity for the separation of N-blocked amino acids, typical acidic analytes of the congener weak anion exchanger CSP, could largely be conserved while results on the elution order and the influence of the N-derivatizing group indicate a principally unchanged binding mechanism as it is described for cinchona carbamate type CSPs. Enantioselectivity towards chiral amines could also be achieved with the novel zwitterionic CSPs, again in a comparable manner to the previously reported parent SCX CSP.

Additionally, the invention enables enantioseparations of zwitterionic analytes via a double ion pairing process: Base-line separation or at least partial separation of 40 amino acids of various types and structures as well as dipeptides could be achieved with novel zwitterionic CSPs 1-5. A general separation concept could be derived thereof where the underlying molecular recognition mechanism is dominated by the alkaloid substructure of the SO but separation can only occur in combination and with the support, respectively, of the acidic side chain. Among the zwitterionic CSPs herein investigated, CSP 3 provided the most and best enantioseparations of acids, bases, and amino acids.

REFERENCES

[1] N. M. Maier, P. Franco, W. Lindner, J. Chromatogr. A 906 (2001) 3.
[2] I. Ilisz, R. Berkecz, A. Peter, J. Sep. Sci. 29 (2006) 1305.
[3] E. J. Franco, H. Hofstetter, O. Hofstetter, J. Sep. Sci. 29 (2006) 1458.
[4] J. Haginaka, J. Chromatogr. A 906 (2001) 253.
[5] M. Lämmerhofer, W. Lindner, in E. Grushka, N. Grinberg (Eds.), Liquid Chromatographic Enantiomer Separation and Chiral Recognition by Cinchona Alkaloid-Derived Enantioselective Separation Materials. CRC Ress, Taylor & Francis Group, Boca Raton, 2008, p. 1.
[6] M. Lämmerhofer, W. Lindner, J. Chromatogr. A 741 (1996) 33.

[7] E. Zarbl, M. Lammerhofer, A. Woschek, F. Hammerschidt, C. Parenti, G. Cannazza, W. Lindner, J. Sep. Sci. 25 (2002) 1269.
[8] E. Tobler, M. Lammerhofer, F. Wuggenig, F. Hammerschmidt, W. Lindner, Electrophoresis 23 (2002) 462.
[9] S. Constantin, W. Bicker, E. Zarbl, M. Lammerhofer, W. Lindner, Electrophoresis 24 (2003) 1668.
[10] D. Hebenstreit, W. Bicker, M. Lammerhofer, W. Lindner, Electrophoresis 25 (2004) 277.
[11] B. Preinerstorfer, W. Lindner, M. Lammerhofer, Electrophoresis 26 (2005) 2005.
[12] B. Preinerstorfer, D. Lubda, W. Lindner, M. Lammerhofer, J. Chromatogr. A 1106 (2006) 94.
[13] C. V. Hoffmann, M. Lammerhofer, W. Lindner, J. Chromatogr. A 1161 (2007) 242.
[14] C. L. Wang, D. W. Armstrong, D. S. Risley, Analytical Chemistry 79 (2007) 8125.
[15] P. N. Nesterenko, P. R. Haddad, Analytical Sciences 16 (2000) 565.
[16] W. Z. Hu, P. R. Haddad, Trac-Trends in Analytical Chemistry 17 (1998) 73.
[17] W. Z. Hu, T. Takeuchi, H. Haraguchi, Analytical Chemistry 65 (1993) 2204.
[18] W. Z. Hu, H. Tao, H. Haraguchi, Analytical Chemistry 66 (1994) 2514.
[19] W. Z. Hu, H. Haraguchi, Analytical Chemistry 66 (1994) 765.
[20] L. W. Yu, R. A. Hartwick, Journal of Chromatographic Science 27 (1989) 176.
[21] L. W. Yu, Floyd, T. R., Hartwick, R. A., Journal of Chromatographic Science 24 (1986) 177.
[22] P. N. Nesterenko, A. I. Elefterov, D. A. Tarasenko, O. A. Shpigun, J. Chromatogr. A 706 (1995) 59.
[23] C. Viklund, A. Sjogren, K. Irgum, I. Nes, Analytical Chemistry 73 (2001) 444.
[24] W. Jiang, G. Fischer, Y. Girmay, K. Irgurn, J. Chromatogr. A 1127 (2006) 82.
[25] M. H. Hyun, J. S. Jin, W. J. Lee, J. Chromatogr. A 822 (1998) 155.
[26] M. H. Hyun, J. Sep. Sci. 26 (2003) 242.
[27] V. A. Davankov, J. Chromatogr. A 666 (1994) 55.
[28] A. Sztojkov-Ivanov, L. Lazar, F. Fulop, D. W. Armstrong, A. Peter, Chromatographia 64 (2006) 89.
[29] V. A. Davankov, A. S. Bochkov, A. A. Kurganov, P. Roumeliotis, K. K. Unger, Chromatographia 13 (1980) 677.
[30] R. Berkecz, A. Sztojkov-Ivanov, I. Ilisz, E. Forro, F. Fulop, M. H. Hyun, A. Peter, J. Chromatogr. A 1125 (2006) 138.
[31] R. Berkecz, R. Torok, I. Ilisz, E. Forro, F. Fulop, D. W. Armstrong, A. Peter, Chromatographia 63 (2006) S37.
[32] A. Peter, R. Berkecz, F. Fulop, Journal of Peptide Science 12 (2006) 234.
[33] H. Gika, M. Lämmerhofer, I. Papadoyannis, W. Lindner, Journal of Chromatography B 800 (2004) 193.
[34] R. Sardella, M. Lämmerhofer, B. Natalini, W. Lindner, Chirality 20 (2008) 571.
[35] A. Mandl, L. Nicoletti, M. Lämmerhofer, W. Lindner, J. Chromatogr. A 858 (1999) 1.
[36] R. Nogueira, M. Lammerhofer, N. M. Maier, W. Lindner, Analytica Chimica Acta 533 (2005) 179.
[37] F. M. Cordero, M. Cacciarini, F. Machetti, F. de Sarlo, Eur. J. Org. Chem. (2002) 1407.
[38] C. Czerwenka, M. Lammerhofer, W. Lindner, J. Sep. Sci. 26 (2003) 1499.
[39] P. Franco, M. Lammerhofer, P. M. Klaus, W. Lindner, J. Chromatogr. A 869 (2000) 111.
[40] Kricheld. Hr, Annalen Der Chemie-Justus Liebig 763 (1972) 17.
[41] K. Gyimesi-Forrás, K. Akasaka, M. Lämmerhofer, N. M. Maier, T. Fujita, M. Watanabe, N. Harada, W. Lindner, Chirality 17 (2005) S134.
[42] W. Bicker, D. Hebenstreit, M. Lämmerhofer, W. Lindner, Electrophoresis 24 (2003) 2532.

The invention claimed is:

1. An enantioselective zwitterionic ion-exchange material comprising:
a chiral selector component comprising at least one cation exchange group and at least one anion exchange group; and
a carrier carrying said chiral selector component,
wherein said chiral selector component comprises at least one chiral linker moiety to connect said at least one cation ion exchange group and said at least one anion exchange group in a non-macrocyclic fashion,
wherein said chiral linker moiety contains at least one π-π interaction site,
wherein said at least one anion exchange group comprises a quinine or quinidine residue, and
wherein said at least one cation exchange group comprises a cyclohexanesulfonic group.

2. The enantioselective zwitterionic ion-exchange material of claim 1, wherein said at least one cation exchange group has a pka less than 5.5, and wherein said at least one anion exchange group has a pka greater than 8.0.

3. The enantioselective zwitterionic ion-exchange material of claim 1, wherein said at least one cation exchange group has a pka less than 3.0 and said at least one anion exchange group has a pka greater than 8.0.

4. The enantioselective zwitterionic ion-exchange material of claim 1, wherein said selector compound contains at least two acidic groups with pka values less than 5.5 and at least one basic group with a pka greater than 8.0.

5. The enantioselective zwitterionic ion-exchange material of claim 1, wherein said ion-exchange material comprises a compound of formula $I_{CSP}$ attached to the carrier, which is designated as CARRIER:

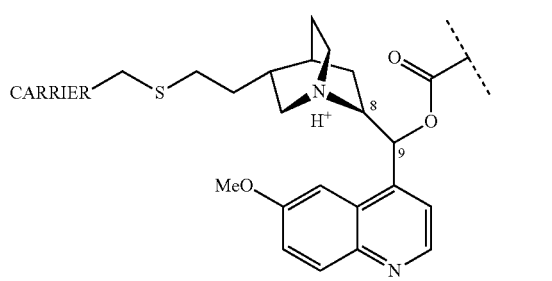

$I_{CSP}$

6. The enantioselective zwitterionic ion-exchange material of claim 5, wherein the following group is attached such that $I_{CSP}$ is CSP 3:

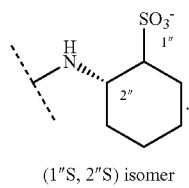

(1″S, 2″S) isomer

7. The enantioselective zwitterionic ion-exchange material of claim 5, wherein the following group is attached such that $I_{CSP}$ is CSP 4:

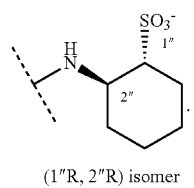

(1″R, 2″R) isomer

8. The enantioselective zwitterionic ion-exchange material of claim 1, wherein the carrier is thiol-modified silica gel.

9. A method for chromatographic resolution of enantiomers, comprising:
providing an enantioselective zwitterionic ion-exchange material as in claim 1;
contacting said enantioselective zwitterionic ion-exchange material with a mixture of enantiomeric compounds selected from the group consisting of chiral acid compounds, chiral amine compounds, and chiral zwitterionic compounds; and
said enantioselective zwitterionic ion-exchange material at least partially resolving said mixture of enantiomeric compounds by chromatographically separating a first chiral compound from a second chiral compound that is an enantiomer of the first chiral compound.

10. The method of claim 9, wherein at least partially resolving said mixture of enantiomeric compounds comprises chromatographically separating chiral acid compounds.

11. The method of claim 9, wherein at least partially resolving said mixture of enantiomeric compounds comprises chromatographically separating chiral amine compounds.

12. The method of claim 9, wherein at least partially resolving said mixture of enantiomeric compounds comprises chromatographically separating chiral zwitterionic compounds.

13. The method of claim 12, wherein at least partially resolving said mixture of enantiomeric compounds comprises chromatographically separating chiral amino acid compounds.

14. The method of claim 12, wherein at least partially resolving said mixture of enantiomeric compounds comprises chromatographically separating chiral peptide compounds.

15. An enantioselective zwitterionic ion-exchange material comprising:
a chiral selector component comprising a compound of formula $I_{CSP}$:

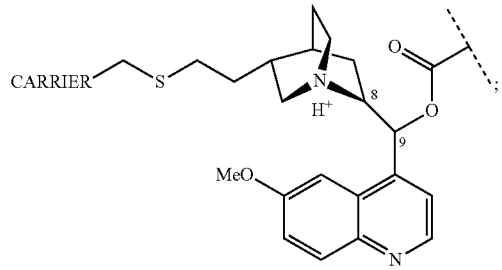

a carrier carrying said chiral selector component, which is designated as CARRIER,
wherein attached is a group selected from

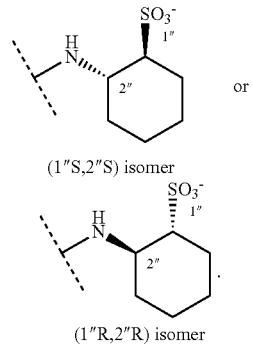

* * * * *